United States Patent [19]

Newitter

[11] 4,261,697
[45] Apr. 14, 1981

[54] EVACUATING RUBBER DAM FRAME

[76] Inventor: David A. Newitter, 1 Nathan Hale Dr., Setauket, N.Y. 11733

[21] Appl. No.: 121,841

[22] Filed: Feb. 15, 1980

[51] Int. Cl.³ .............................................. A61C 5/14
[52] U.S. Cl. ................................................... 433/137
[58] Field of Search ................... 433/136, 137, 91, 93, 433/96

[56] References Cited

U.S. PATENT DOCUMENTS

| | | | |
|---|---|---|---|
| 3,396,468 | 8/1968 | Dayhoff | 433/93 |
| 3,772,790 | 11/1973 | Swan-Gett et al. | 433/136 |
| 3,781,994 | 1/1974 | Hesselgrea | 433/136 |

Primary Examiner—Robert Peshock
Attorney, Agent, or Firm—Edward R. Freedman

[57] ABSTRACT

An evacuating rubber dam frame for supporting a rubber dam adjacent to the mouth of a dental patient comprises a frame containing a hollow portion, said hollow portion having means for gathering in any fluid collected by said rubber dam, and means for removal of the fluid gathered into said hollow portion.

35 Claims, 43 Drawing Figures

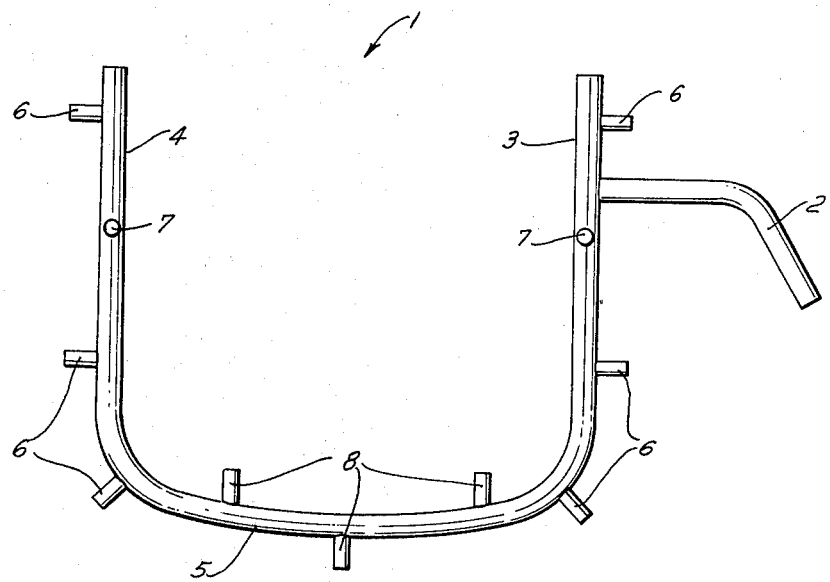
FIG. 1
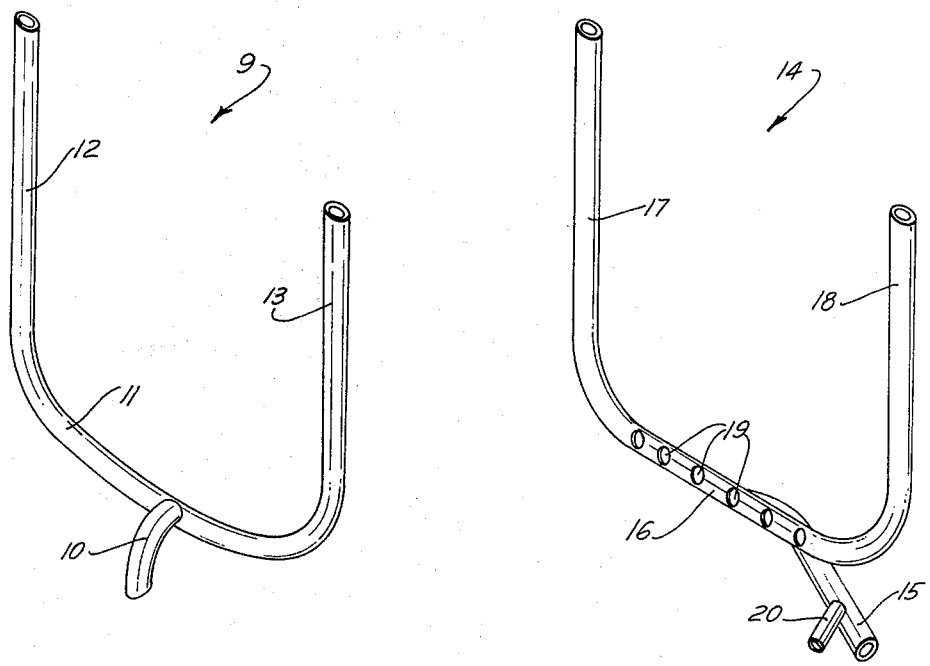
FIG. 2
FIG. 3

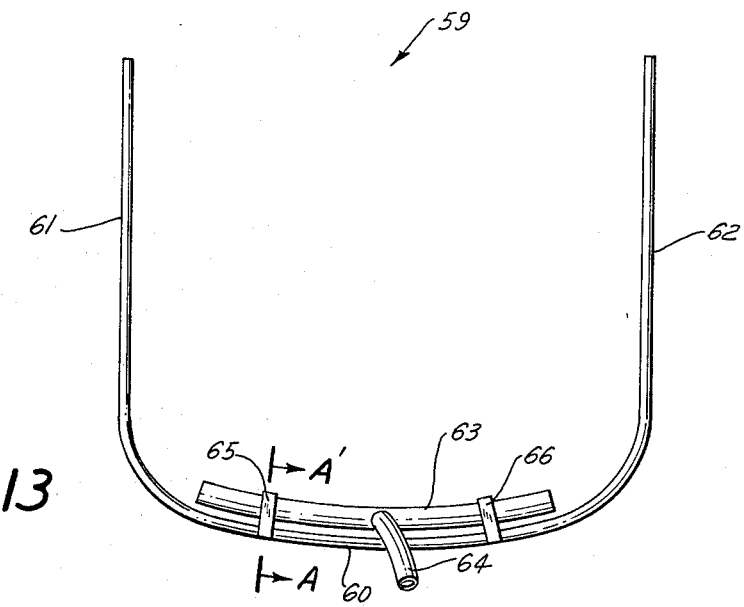
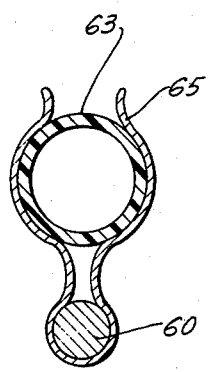
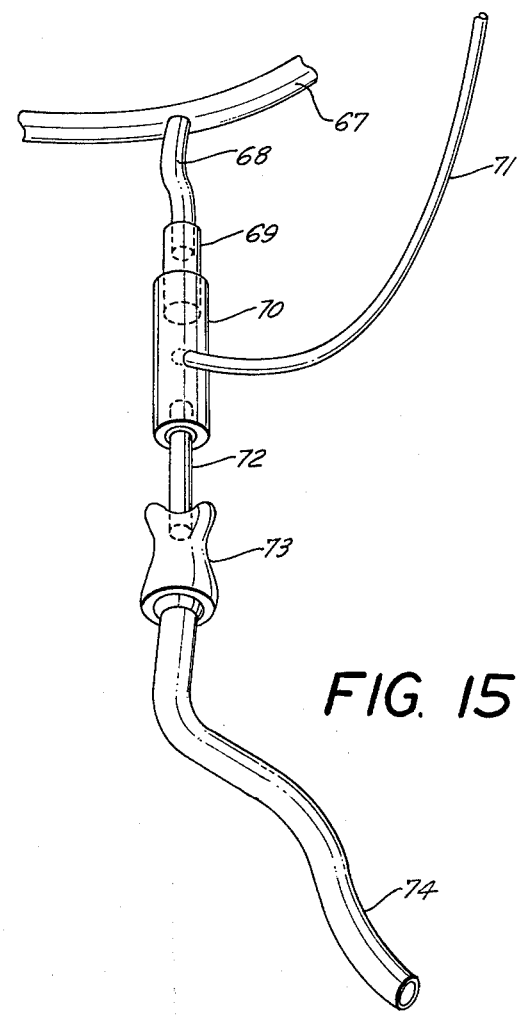
FIG. 13
FIG. 14
FIG. 15

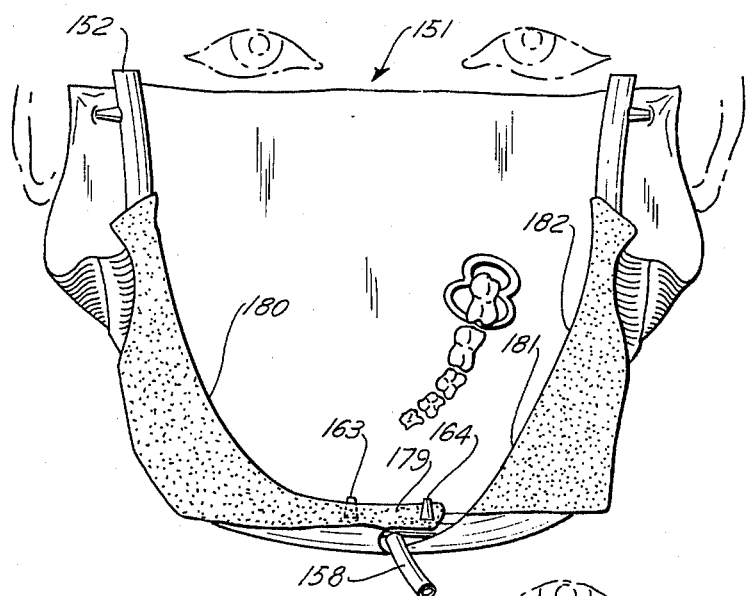
FIG. 34
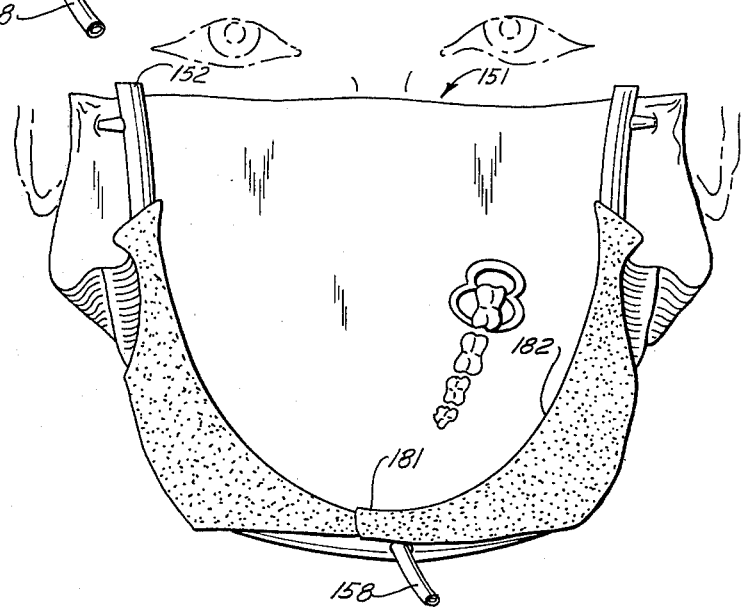
FIG. 35
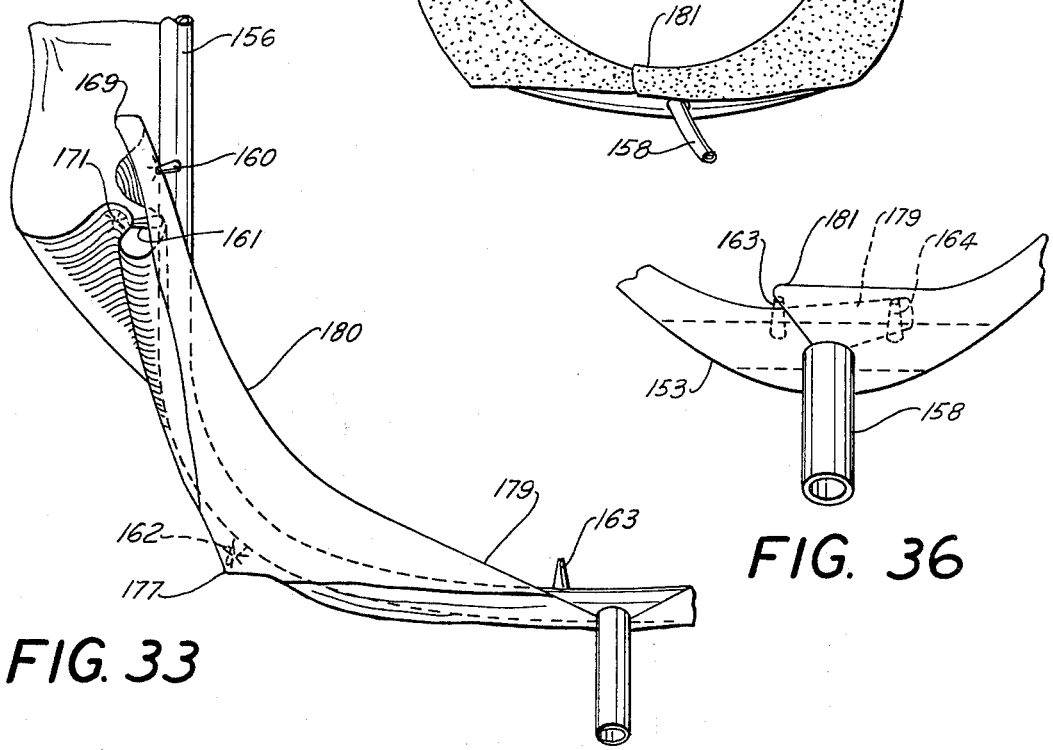
FIG. 36
FIG. 33

EVACUATING RUBBER DAM FRAME

BACKGROUND OF THE INVENTION

A rubber dam is a device used for the isolation of teeth for purposes of dental treatment. The rubber dam is made of a thin sheet of flexible material. Holes are placed in the rubber dam with a hole punch and individual teeth are poked through these individual holes. A clamp placed upon a tooth is usually used to help hold the dam in place and is most often placed upon the tooth isolated farthest toward the back of the mouth.

The rubber dam is frequently stretched on a frame. The frame functions as a holder of the dam so that the dam does not move into the field of dental interest. On some frames are small barb-like structures for engaging the rubber dam.

During various steps in the process of dental treatment with the rubber dam held in place by the rubber dam frame, so as to isolate a part of the patient's mouth, this isolated part of the patient's mouth tends to quickly fill up with fluids. These fluids include water used to cool a high speed drill, antiseptic solution, irrigation solution, saliva, blood, aerosol spray mists, topical anesthesia, etc.

It is therefore necessary to promptly remove these fluids and to take precautions to prevent the overflow of liquids onto the patient and to prevent the inhalation of aerosol spray mist by the patient and others present in the room.

Attempts have been made in the past to overcome these difficulties; and prior proposals are as follows.

From the *Journal of the American Dental Association*, Volume 55, in the December 1957 issue, pages 804 to 808, is found the article, "Debridement in Endodontics" by Julius G. Godwin, D.D.S. In this article is a discussion of using a self-retaining drainage tube which is anchored in the rubber dam pouch or pocket formed when the lower portion of the rubber dam is wrapped around a metal frame holder. This drainage tube is anchored by means of an adapter inserted from below through a hole made into the rubber dam pouch. The other end of the drainage tube can be connected to a saliva ejector which will provide suction for evacuation of certain liquids.

From *Journal of Dentistry for Children*, Volume 32 #2, 1965, pages 112 to 117, is found an article by R. V. Brown, D.D.S., which discusses "Bacterial Aerosols Generated by Ultra High-Speed Cutting Instruments".

From *A Manual of Operative Dentistry*, in the 1961 Edition, by H. M. Pickard, F.D.S., is found the teaching of a rubber dam used with a completely solid rubber dam frame. This frame has two vertical arms with each arm having the free end portion thereof, not connected to the horizontal arm, bent laterally and curved outwardly away from the face of the dental patient.

From *Dental Digest*, Volume 71 Number 2, in the February 1965 issue, pages 56 to 59, is found the article, "Fixed Internal Splinting of Anterior Teeth" by Julius G. Godwin, D.D.S. On page 57 is a brief discussion of a rubber dam and frame plus drainage tube similar to that set forth above by the same author in his article found in the *Journal of the American Dental Association*, December 1957, pages 804 to 808.

From *Journal of Prosthetic Dentistry*, Volume 28 Number 4, in the October 1972 issue, pages 391 and 395, is found the article, "Access—the Key to Success" by Hunter A. Brinker, D.D.S. In this article is a discussion of using a rubber dam with the Endon style frame. This style frame has a rigid extension fastened to the horizontal bar which provides a pouch when the rubber dam is drawn around it.

From *Operative Dental Surgery*, in the 1972 Edition, pages 58 to 59, by J. J. Messing, D.D.S., et al, is a discussion of various rubber dam clamps and frames.

From *The Conservation of Teeth*, First Published 1973, in Chapter 11, pages 210, 211 and 213 to 216 is found the article "Control of Fluids in the Mouth" by J. D. Eccles, Ph.D., et al. In this article is a discussion of an integral dam and frame used during certain dental treatments.

From *Principles and Practice of Operative Dentistry*, by Gerald T. Charbeneau, D.D.S., et al, in the 1975 Edition, at pages 200, 201, and 227 is found a discussion of using an Endon frame with a rubber dam during certain dental procedures.

From *A Manual of Operative Dentistry*, in the Fourth Edition 1976, pages 34 to 37, is found the article, "The Control of Moisture, Pain, and Trauma in Operative Procedures" by H. M. Pickard F.D.S. In this article is a discussion of using a rubber dam with a rubber dam frame to control moisture in the mouth.

U.S. Pat. No. De. 221,338 issued Aug. 3, 1971, to Brave teaches an ornamental design for a completely solid U-shaped dental dam frame in which the horizontal arm is solid and imperforate.

U.S. Pat. No. 663,507 issued Dec. 11, 1900, to Megular teaches a dental rubber dam holder comprising a circular, dished or deflected, continuous frame, having a base portion curved outwardly to prevent inpingement upon the chain of a dental patient.

U.S. Pat. No. 682,308 issued Sept. 10, 1901, to Young teaches a rubber dam holder formed of a jointless U-shaped completely solid imperforate body portion having engaging points for the rubber dam and having a base portion curved outwardly to prevent impingement upon the chin of a dental patient.

U.S. Pat. No. 730,128 issued June 2, 1903, to Jordan teaches a saliva ejector having buccal and lingual tubular drainage portions with each portion having a saliva inlet, and the inlet of the buccal portion having a manually operable valve, whereby this valve can be maintained normally closed and can be opened at intervals to permit the removal of accumulated liquid from the buccal surface of the mouth.

U.S. Pat. No. 1,292,133 issued Jan. 21, 1919, to Stoughton teaches a rubber dam frame and a plurality of cleats on the outer sides of the frame, each cleat including two oppositely extended considerably elongated point portions aligned with the adjacent part of the frame and having blunt ends, whereby a rubber dam may be laid over the frame and immediately adjacent local portions stretched over the cleats under tension longitudinally of the cleats to be frictionally held thereon by each cleat individually.

U.S. Pat. No. 3,049,806 issued Aug. 21, 1962, to Cofresi teaches a dental saliva ejector comprising an ejector head containing a tubular member having its ends disposed in side-by-side relation, a connector detachably secured to said ends and retaining them in fixed position and establishing communication between a suction conduit and said tubular member, said tubular member being curved between its ends to provide a frame for enclosing a set of teeth and having inlet orifices opening to both sides of a set of teeth and for educting saliva accumulating on both sides of said set of teeth, and an adjustable brace secured to said tubular member and rigidifying the latter and constituting a tongue depressor.

U.S. Pat. No. 3,091,859 issued June 4, 1963, to Baughan teaches a dental saliva ejector comprising a main suction tube having a first hook-like portion engageable over the lower incisor teeth and adapted to rest on the floor of the mouth on the lingual side of the lower gum during use, and having a second portion horizontal tube section structured to conform to the mouth in the buccal and labial cheek folds.

U.S. Pat. No. 3,406,452 issued Oct. 22, 1968, to McConville teaches a dental dam frame comprising a rigid U-shaped frame having a horizontal base portion between two vertical stem portions. The base portion is curved outwardly away from the longitudinal axes of the stem portions such that the base portion does not impinge upon the chin of a dental patient when said U-shaped frame is properly positioned for use. The ends of the stem portions remote from the base portion are bent laterally outwardly from one another.

U.S. Pat. No. 3,735,491 issued May 29, 1973, to Pabalan teaches a device for preventing the discharge of aerosols from the mouth of a patient during a dental procedure. This device combines a cheek retractor with a means for creating a high vacuum field within the oral cavity for direct aspiration of aerosols, and wherein the stream of outside air entering the patient's mouth to fill the vacuum intercepts any outgoing particles which may have initially escaped aspiration.

U.S. Pat. No. 3,781,994 issued Jan. 1, 1974, to Hesselgren teaches a dental device comprising a rubber dam and an inflatable hollow tubular frame integral with the rubber dam. There is a conduit means communicating with the interior of the hollow tubular frame by which this frame may be inflated. The inflatable hollow tubular frame forms a collecting pocket about the rubber dam; and there is at least one drain nipple communicating with this collecting pocket for connection with means to evacuate the collecting pocket. The dental device of Hesselgren is so constructed that it is soft and flexible so as to cause a minimum amount of inconvenience when applied to the dental patient. Since the frame piece of Hesselgren is to be inflated with compressed air through an inflation nipple, evacuation holes could not possibly be present in the rear side of the frame piece, because these holes would permit the compressed air to escape and would result in a deflationary collapse of the previously inflated frame of Hesselgren. According to Hesselgren, the frame cannot be a rigid frame, since it must be soft and flexible for reasons of patient comfort, and since this structure must be flexible to be inflatable. For all these reasons, the Hesselgren frame does not itself function to evacuate through the frame fluids which are adjacent to the frame after these fluids had been first collected by the rubber dam.

OBJECTS OF THE INVENTION

It is an object of the present invention to provide a rubber dam frame which will support a rubber dam used during a dental procedure, and which will simultaneously evacuate through the frame, fluids which are adjacent to the frame, after these fluids had first been collected by the rubber dam.

It is another object of the present invention to provide an evacuating rubber dam frame for supporting a rubber dam adjacent to the mouth of a dental patient comprising a frame containing a hollow portion, said hollow portion having means for gathering in any fluid collected by said rubber dam, and means for removal of fluid gathered into said hollow portion.

It is a further object of the present invention to provide an evacuating rubber dam frame for supporting a rubber dam adjacent to the mouth of a dental patient comprising two vertical arms, a hollow horizontal arm connected to the bottom part of both of said vertical arms, said hollow horizontal arm having at least one evacuation opening in the rear of said horizontal arm for gathering in any fluid collected by said rubber dam, and a hollow drainage tube attached to one of said arms for removal of fluid gathered into said hollow horizontal arm.

These and further objects of the present invention will become more apparent as the description of the invention proceeds.

THE DRAWINGS

The present invention will also be described by reference to the following drawings which are not to be deemed limitative of the invention in any manner thereof.

FIG. 1 shows a front view of an evacuating rubber dam frame having a hollow drainage tube attached to one of the vertical arms.

FIG. 2 shows a front perspective view of an evacuating rubber dam frame having a hollow drainage tube attached to the horizontal arm.

FIG. 3 shows a rear perspective view of an evacuating rubber dam frame having a hollow drainage tube attached to the horizontal arm.

FIG. 13 shows a front view of an evacuating rubber dam frame having two horizontal arms.

FIG. 14 shows a section view along line A—A' of FIG. 13.

FIG. 15 shows a front view of an assembly for connection of a hollow drainage tube with a saliva ejector.

FIG. 33 shows an enlarged front view of part of FIG. 32.

FIG. 34 shows the next step in forming a cross-over seal.

FIG. 35 shows the last step in forming a cross-over seal.

FIG. 36 shows an enlarged front view of the cross-over seal of FIG. 35.

DESCRIPTION OF THE INVENTION

Figure 4:
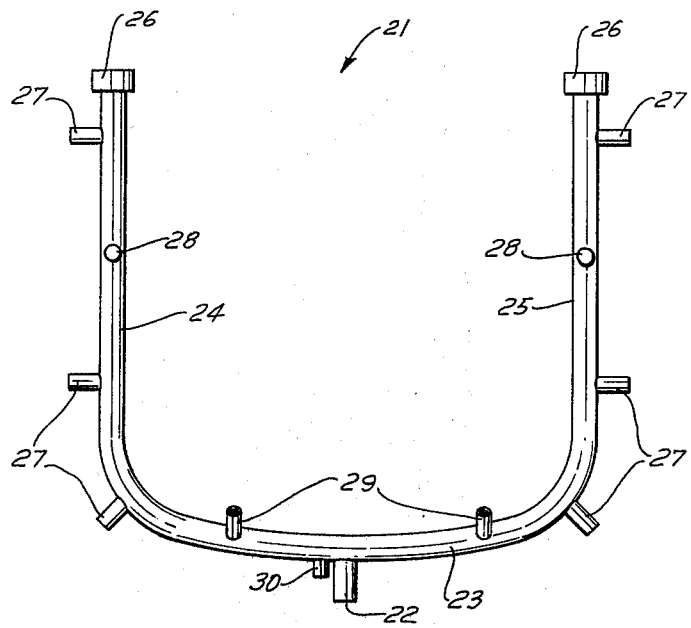
FIG. 4 shows a front view of an evacuating rubber dam frame having a hollow drainage tube attached to the horizontal arm.

The present invention relates to a rubber dam frame which will support a rubber dam used during a dental procedure, and which will simultaneously evacuate through the frame, fluids which are adjacent to the frame, after these fluids had first been collected by the rubber dam.

More particularly, the present invention is directed to an evacuating rubber dam frame for supporting a rubber dam adjacent to the mouth of a dental patient comprising a frame containing a hollow portion, said hollow portion having means for gathering in any fluid collected by said rubber dam, and means for removal of fluid gathered into said hollow portion.

Also the present invention is directed to an evacuating rubber dam frame for supporting a rubber dam adjacent to the mouth of a dental patient comprising two vertical arms, a hollow horizontal arm connected to the bottom part of both of said vertical arms, said hollow horizontal arm having at least one evacuation opening in the rear of said horizontal arm for gathering in any fluid collected by said rubber dam, and a hollow drainage tube attached to one of said arms for removal of fluid gathered into said hollow horizontal arm.

The term, rubber dam, is meant to refer to a thin sheet of flexible material that is impervious to fluids utilized during dental procedures and/or found in the mouth of a dental patient. Thus the rubber dam may be made from elastic materials such as rubber, thermoforming plastics, plastic laminates or any other suitable elastic materials.

The rubber dam frame of the present invention is made by providing a hollow rubber dam frame that can be connected to a suction device, such as a dental saliva ejector, in order to remove fluids, primarily water, that are collected by the rubber dam.

The rubber dam frame need not be of any specified shape as long as the frame is capable of supporting a rubber dam adjacent to the mouth of a dental patient, and is capable of removing fluids through the frame.

Adjacent to the patient's mouth means that the rubber dam surrounds the outside of the patient's mouth, while also fitting within the patient's mouth in order to separate those teeth to be worked on from the rest of the patient's teeth, and in order to isolate those separated teeth from the remainder of the oral cavity.

Thus the shape of the rubber dam frame can be eliptical, circular, polygonal, square, rectangular, or U-shaped, with U-shaped being preferred.

That portion of the rubber dam frame, through which a fluid is to flow to be withdrawn, must be hollow. Thus the hollow portion of the rubber dam frame would include that part of the frame which is in contact with the fluid collected by the rubber dam, as well as that part of the frame through which the flowing fluid is to be removed. Therefore a part of the rubber dam frame can be solid provided no fluid is to flow therethrough.

Regarding the U-shaped evacuating rubber dam frame, which is the preferred embodiment, this frame is comprised of two vertical arms with a horizontal arm connected to the bottom part of both of these vertical arms. The U-shaped frame may be manufactured by starting with a straight hollow continuous rigid metal tube such as copper tubing, or rigid plastic tube such as polyethylene tubing, and then bending the straight tube into a U-shaped tube. Also the frame can be made in one or separate units by casting a material such as metal or plastic into an appropriately shaped mold.

At least one round hole, or alternatively a slit-like hole, creating an evacuation opening, is then formed, or punched, into the rear side of the horizontal portion of the hollow continuous rigid tube frame. it is also possible to provide many round holes, or many slit-like openings, creating many evacuation openings, in the rear side of the horizontal portion of the hollow continuous rigid tube frame.

The term, rear side, refers to that side of the frame which is nearest to the face of the dental patient when the frame is being used during a dental procedure.

Generally, these evacuation openings serve as a means for gathering into the hollow portion of the frame any fluid collected by the rubber dam. For the U-shaped frame they serve as a means for gathering into the hollow horizontal arm any fluid which has been collected by the rubber dam, in the pocket formed between the rubber dam and the lowest portion of the frame, which is the horizontal arm of the U-shaped frame.

The gathered in fluid must then be removed from the hollow inside of the rubber dam frame. This is accomplished by providing a means for removal of the fluid gathered into the hollow portion of the horizontal arm. An example of such a removal means is a hollow rigid, or flexible, drainage tube which is attached to one of the three arms of the U-shaped frame.

If the hollow rigid drainage tube is attached to the hollow horizontal arm, then this tube can be attached to the front side of, and in the front central portion of, the horizontal arm, so as not to contact the face of the dental patient. The hollow tube opens into the hollow horizontal arm in such a manner, that there is an uninterrupted channel through which the gathered in fluid can exist from the horizontal arm. Ordinarily, the fluid will exit under gravity flow conditions, since the drainage tube opening into the horizontal arm is positioned substantially opposite to the evacuation openings and is positioned at a level somewhat lower than the level at which the evacuation openings are located in the rear of the horizontal arm. However, as a preferred embodiment, the drainage tube is connected to a suction device, such as a saliva ejector, so that the removal means becomes a suction drainage tube.

If the hollow rigid drainage tube is attached to one of the two rigid vertical arms of the U-shaped frame, then this one rigid vertical arm must contain a hollow portion which connects the hollow horizontal arm to the hollow drainage tube. This is to provide an uninterrupted channel through which the gathered in fluid can flow and can exit from the U-shaped frame. Because the gathered in fluid must flow upwardly through at least a part of the vertical arm, it will be necessary for the drainage tube to be connected to a suction device, such as a saliva ejector.

If the hollow drainage tube is attached to the hollow horizontal arm of a U-shaped frame, then each of the two vertical arms of the U-shaped frame can be a solid arm, since no fluid is evacuated therethrough. Also each of the two vertical arms can be a hollow arm, even though the hollow drainage tube is attached to the hollow horizontal arm. If the hollow drainage tube is attached to one of the two vertical arms of the U-shaped frame, then this one vertical arm to which it is attached must be hollow, whereas the other vertical arm can be either solid or hollow.

In one embodiment of the U-shaped evacuating rubber dam frame, each of the two vertical arms is continuously connected to the hollow horizontal arm to form a unitary frame.

In another embodiment of the U-shaped evacuating rubber dam frame, there are attachment means for removably coupling each of the two vertical arms to the hollow horizontal arm. Various examples of attachment means include screw thread means, friction joint means and elbow joint means.

In another embodiment of the U-shaped evacuating rubber dam frame, at least one of the two vertical arms is of a thickness different from that of the hollow horizontal arm.

In another embodiment of the U-shaped evacuating rubber dam frame, the two vertical arms are parallel to each other and are in one plane, and the hollow horizontal arm is in the same plane as the two vertical arms.

In a different embodiment, the two vertical arms are parallel to each other and are in a first plane, and the hollow horizontal arm is curved outwardly away from this first plane. Thus the horizontal arm will not contact the face of the dental patient during use of the frame. Also it is possible to have an embodiment wherein the ends of the vertical arms remote from the horizontal arm are bent laterally outwardly from one another. This creates a frame being a U-shaped member which is contoured to be retractable against a portion of the face of the dental patient surrounding the patient's mouth.

Usually there are rubber dam retention means, such as cleats or barbs, located on the two vertical arms of the U-shaped frame and on the hollow horizontal arm of the U-shaped frame, for engaging the rubber dam. Assume that the drainage tube is attached to the horizontal arm. In this embodiment, there are barbs so structured and arranged on the two vertical arms and on the hollow horizontal arm that the rubber dam when engaging these barbs provides a cross-over seal around the suction drainage tube at the location at which the suction drainage tube is attached to the hollow horizontal arm.

Again assume that the drainage tube is attached to the horizontal arm of the U-shaped frame. In a different embodiment, there are barbs only on the two vertical arms for engaging a rubber dam. In this embodiment, the rubber dam has a hole in the lower portion thereof positioned to receive the hollow drainage tube, with the hole being of slightly smaller inner diameter than the outer diameter of the suction drainage tube. These barbs are so structured and arranged on the two vertical arms, that when the hollow drainage tube is inserted through the hole in the rubber dam, that the rubber dam when engaging these barbs provides a cupped selfseal around the suction drainage tube at the location at which said suction drainage tube is attached to the hollow horizontal arm.

Assume that the drainage tube is attached to one of the vertical arms of the U-shaped frame. There are barbs on the two vertical arms and on the horizontal arms for engaging a rubber dam. In this case, the barbs are so structured and arranged, that the rubber dam when engaging these barbs provides a pocket seal around the hollow horizontal arm.

In still another embodiment of the U-shaped evacuating rubber dam frame, there are two vertical arms and two horizontal arms arranged as follows. The first horizontal arm is an imperforate horizontal arm, preferably solid, without any openings therein, such that this inperforate arm cannot gather in any fluid collected by the rubber dam. This imperforate horizontal arm is connected to the bottom part of both of the vertical arms. Preferrably each of the two vertical arms is continuously connected to the imperforate horizontal arm to form a unitary frame. The second horizontal arm is a hollow horizontal arm having at least one evacuation opening in the rear of said hollow horizontal arm for gathering in any fluid collected by the rubber dam. A hollow drainage tube is attached to the hollow horizontal arm for removal of fluid gathered into the hollow horizontal arm. Preferrably the drainage tube is connected to a suction device, such as a saliva ejector. Coupling means, such as clip means, attach the hollow horizontal arm to the imperforate horizontal arm.

In a still further embodiment of the U-shaped evacuating rubbe dam frame, the hollow horizontal arm further comprises a joint means for permitting the folding, or bending, of the frame.

One type of joint means comprises a flexible joint means such as a pivot joint, an elastic joint or a flexible conduit joint. The flexible joint means permits the folding of the frame without the necessity of first disassembling the frame. Such a pivot joint could be designed into the hollow horizontal arm, whereas the elastic joint or the flexible conduit joint could be fashioned as a segment of the hollow horizontal arm.

Another type of joint means comprises an assembly joint means for assembling and disassembling the frame, so as to permit the folding of the frame. Preferably the assembly joint means is a sleeve joint selected from the group comprising an out-of-round sleeve joint, a polygonal sleeve joint such as a quintagonal male-female sleeve joint, an internally slotted sleeve joint and an externally slotted sleeve joint.

Each type of joint means, both flexible and assembly, has the common characteristic that it prevents the two parts of the frame from rotating around each other. The use of the joint means has the added advantages that the evacuating rubber dam frame can be folded, allowing the side of the frame not retained by a rubber dam clamp, to be bent back upon itself. This permits the easy entrance into the mouth of a dental patient, for example, for the giving of additional local anesthetic solution to the patient, or for the taking of X-rays.

There is an additional embodiment that can be incorporated into any U-shaped, eliptical, circular, square, rectangular or polygonal shaped evacuating rubber dam frame, provided all of the arm members of the frame are hollow and are continuously connected together. In this embodiment there is at least one evacuation opening in that part of the frame which is in contact with the fluid collected in the pocket of the rubber dam. Also in this embodiment are means for removal of aerosol spray mists, such as additional evacuation openings, or holes, in the other member arms of the frame, with these additional evacuation openings positioned into those surfaces of the frame that face the work area. This work area includes the area adjacent to the rubber dam above the fluid collection pocket and adjacent to the rubber dam frame above the fluid collection pocket when used during a dental procedure. When the hollow drainage tube is connected to a suction device, these additional evacuation holes function to more completely evacuate aerosol spray mists from the work area where these aerosol spray mists are created. Thus this embodiment can help to effectively reduce inhalation of bacteria containing aerosol spray mists by the patient and others in the room.

Therefore this embodiment has the distinct advantage that the work area can be partially encircled, such as by using the U-shaped frame, or can be fully encircled, such as by using the eliptical, circular, square, rectangular or polygonal shaped frame, with suction evacuation openings to greatly reduce the probability of a patient or of others nearby inhaling bacteria containing aerosol spray mists generated during a dental procedure.

The evacuating rubber dam frame is held in place next to the face of the dental patient by conventional means, such as yarn, dental floss, or elastic band.

Referring now to the drawings, FIG. 1 shows a front view of a U-shaped evacuating rubber dam rigid frame 1 in which a hollow drainage tube 2 is attached to one of the vertical arms 3 of the frame. Connected to the bottom part of vertical arm 3 and to the bottom part of the other vertical arm 4 is hollow horizontal arm 5. The vertical arms are parallel to each other and are in one plane, along with the hollow horizontal arm being in the same plane as the vertical arms. The hollow drainage tube need not necessarily be in the same plane as the vertical arms or the horizontal arm. Located on the vertical arms 3 and 4 are barbs 6 and 7. Barb 6 is representative of those barbs on each vertical arm which lie approximately in the same plane as the two vertical arms. Barb 7 is representative of those barbs on each vertical arm which are approximately perpendicular to the plane of the two vertical arms. Barb 8 is representative of those barbs on the horizontal arm 5 which lie in approximately the same plane as the horizontal arm.

FIG. 2 shows a front perspective view of a U-shaped evacuating rubber dam rigid frame 9 in which a hollow drainage tube 10 is attached to a hollow horizontal arm 11. Hollow horizontal arm 11 is connected to the bottom part of the two vertical arms 12 and 13, which two arms are parallel to each other and are in the same plane. The hollow horizontal arm 11 is in the same plane as that of the two vertical arms 12 and 13. The hollow drainage tube 10 is located at about the center of arm 11 and extends generally anteriorly and inferiorly from frame 9. This permits connection of tube 10 to a suction device, such as a saliva ejector, so that tube 10 does not interfere with access to the dental field of operation.

FIG. 3 shows a rear perspective view of a U-shaped evacuating rubber dam rigid frame 14 in which a hollow drainage tube 15 is attached to a hollow horizontal arm 16. Hollow horizontal arm 16 is connected to the bottom part of the two vertical arms 17 and 18, which two vertical arms are parallel to each other and are in the same plane. The hollow horizontal arm 16 is in the same plane as that of the two vertical arms 17 and 18. Arm 16 has several evacuation openings, or holes, 19 placed into the rear side of this hollow horizontal arm for gathering into arm 16 any fluid collected by the rubber dam. The rear side is that facing the dental patient.

Accessory attachment tube 20 is a hollow tube which is part of the hollow drainage tube 15 and which is positioned on the posterior inferior portion of the tube 15. Tube 20 is usually of smaller diameter than that of tube 15. Tube 20 can be fitted with an extra tube (not shown) for removing fluids such as water from a pocket in the area of the most distal, or posteriorly isolated, tooth fitted with a clamp. This extra tube can be a small plastic tube containing a thin wire for shape retaining purposes.

FIG. 4 shows a front view of a U-shaped evacuating rubber dam rigid frame 21 in which a hollow drainage tube 22 is attached to a hollow horizontal arm 23. Hollow horizontal arm 23 is connected to the bottom part of the two vertical arms 24 and 25. Since arms 24 and 25 are hollow in this embodiment, each has an open top end which is vacuum-tight sealed by means of cap or plug 26. The caps or plugs 26 can be removed when it is desired to flush out the frame 21 for purposes of cleaning or sterilization. The caps or plugs are then replaced so that the suction vacuum is not diminished at the evacuation openings shown in FIG. 6.

Figure 5:
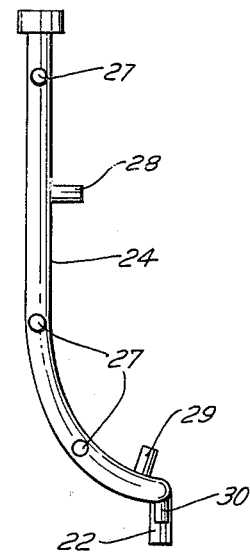
FIG. 5 shows a side view of the evacuating rubber dam frame of FIG. 4.

FIG. 5 shows a side view, looking at arm 24, of the U-shaped evacuating rubber dam frame 21 shown in FIG. 4. The two vertical arms 24 and 25 are parallel to each other and are in the same plane. The hollow horizontal arm 23 is curved outwardly away from this plane. Located on the vertical arms 24 and 25 are barbs 27 and 28. Barb 27 is representative of those barbs on each vertical arm which lie approximately in the same plane as the two vertical arms. Barb 28 is representative of those barbs on each vertical arm which are approximately perpendicular to the plane of the two vertical arms. Barb 29 is representative of those barbs on the horizontal arm 23 which are located on the superior part of arm 23. Barb 30 is representative of those barbs on arm 23 which are located on the inferior, or lower, part of arm 23.

Figure 6:
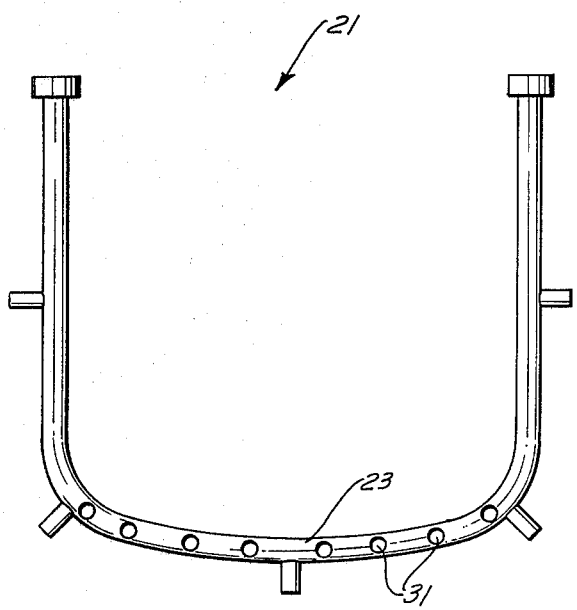
FIG. 6 shows a rear view of the rubber dam frame of FIG. 4.

FIG. 6 shows a rear view of the U-shaped evacuating rubber dam frame 21 shown in FIG. 4. Arm 23 has several evacuation openings, or holes, 31 placed into the rear side of this hollow horizontal arm 23 for gathering into arm 23 any fluid collected by the rubber dam. The rear side is that which faces the dental patient during the dental procedure.

Figures 7, 8:
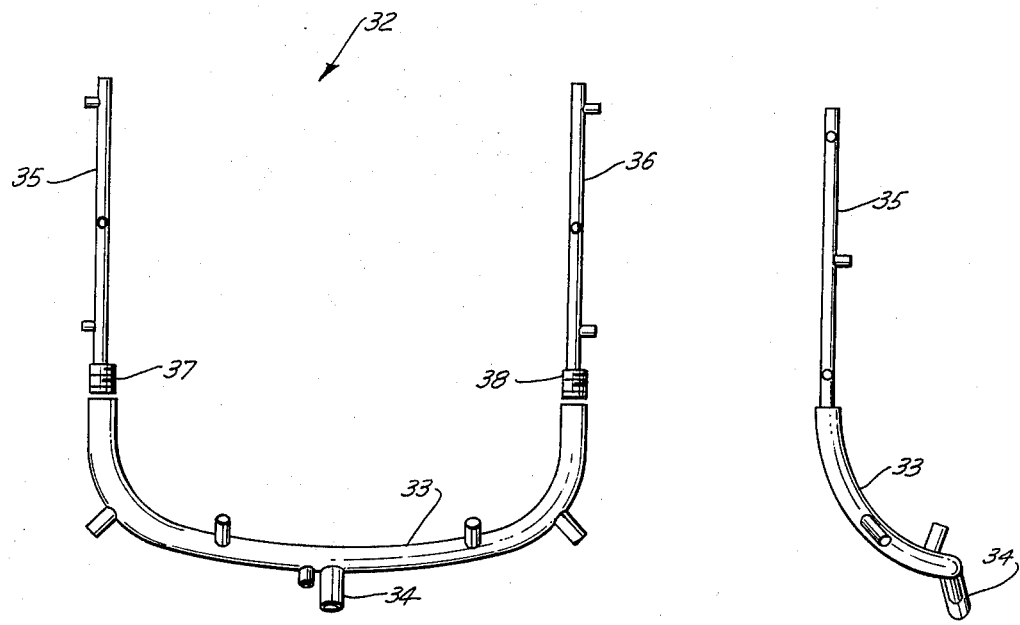
FIG. 7 shows a front view of an evacuating rubber dam frame having coupling means for attaching the vertical arms to the horizontal arm.
FIG. 8 shows a side view of the rubber dam frame of FIG. 7.

FIG. 7 shows a front view of a U-shaped evacuating rubber dam rigid frame 32 having a metal or plastic hollow horizontal arm 33 with a hollow drainage tube 34 attached thereto. Each of the two vertical arms 35 and 36 is a solid, metal or plastic, arm. Attachment means 37 or 38 is located at the lower end of vertical arm 35 or 36, respectively, for removably coupling each solid vertical arm to the hollow horizontal arm 33. Attachment means 37 or 38 is shown to be a screw thread means, but each could be a friction joint means.

FIG. 8 shows a side view, looking at arm 35, of the U-shaped evacuating rubber dam frame 32 shown in FIG. 7. The two vertical arms 35 and 36 are parallel to each other and are in the same plane. The hollow horizontal arm 33 is curved outwardly away from this plane. Attachment means 37 of arm 35 has been tightened into place within the upper end of the horizontal arm 33, so as to removably couple together arms 33 and 35. When it is desired to clean or sterilize frame 32, the vertical arms are uncoupled from, and removed from, the horizontal arm so that each arm can be individually processed. The hollow horizontal arm can then be flushed out.

Figure 9:
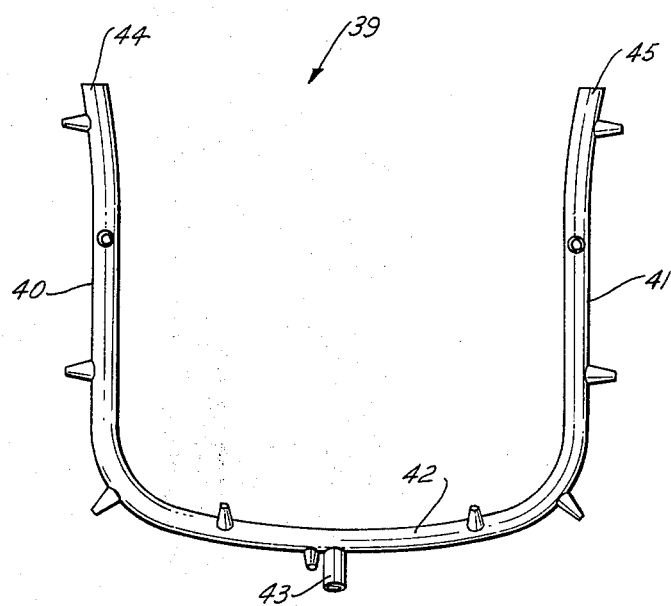
FIG. 9 shows a front view of an evacuating rubber dam frame having a hollow drainage tube attached to the horizontal arm.

FIG. 9 shows a front view of a U-shaped evacuating rubber dam rigid frame 39, constructed as a single unit, with each of the two vertical arms 40 and 41 continuously connected to the hollow horizontal arm 42 to form a unitary frame. Both of the vertical arms can be solid, or both can be hollow, or there can be one solid and one hollow vertical arm. Arm 42 has a hollow drainage tube 43 in the front, with evacuation openings (not shown) in the rear of the horizontal arm. The ends 44 and 45 of the two vertical arms 40 and 41, respectively, remote from the horizontal arm 42 are bent laterally outwardly away from one another.

Figure 10:
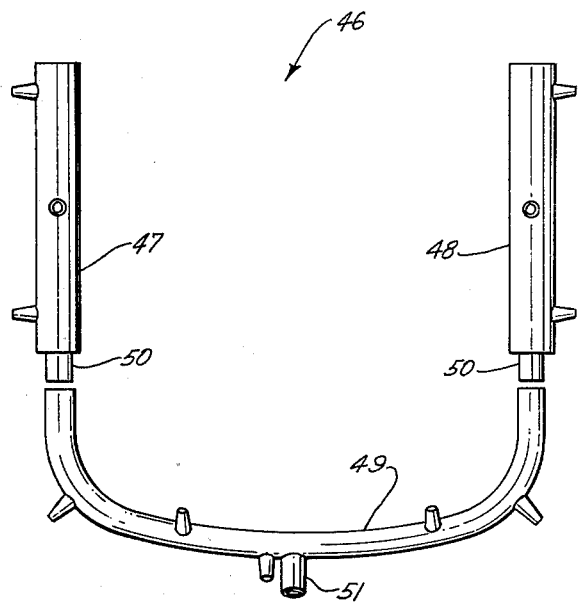
FIG. 10 shows a front view of an evacuating rubber dam frame having three separate arms.

FIG. 10 shows a front view of a U-shaped evacuating rubber dam rigid frame 46 made of three separate arms. Each of the two vertical arms 47 and 48 may be solid or hollow, metal or plastic; and each arm 47 and 48 is of a diameter larger than the diameter of the hollow, metal or plastic, horizontal arm 49. The vertical arms are connected by means of a friction joint 50 to the horizontal arm. Instead of using a friction joint, a screw thread could be utilized for this connection. The horizontal arm has a hollow drainage tube 51 attached to the anterior side, with evacuation openings (not shown) in the posterior side of the horizontal arm. Vertical arms 47 and 48 can be removed from horizontal arm 49 for purposes of internal and/or external cleaning and sterilizing of these three arms.

Figures 11, 12:
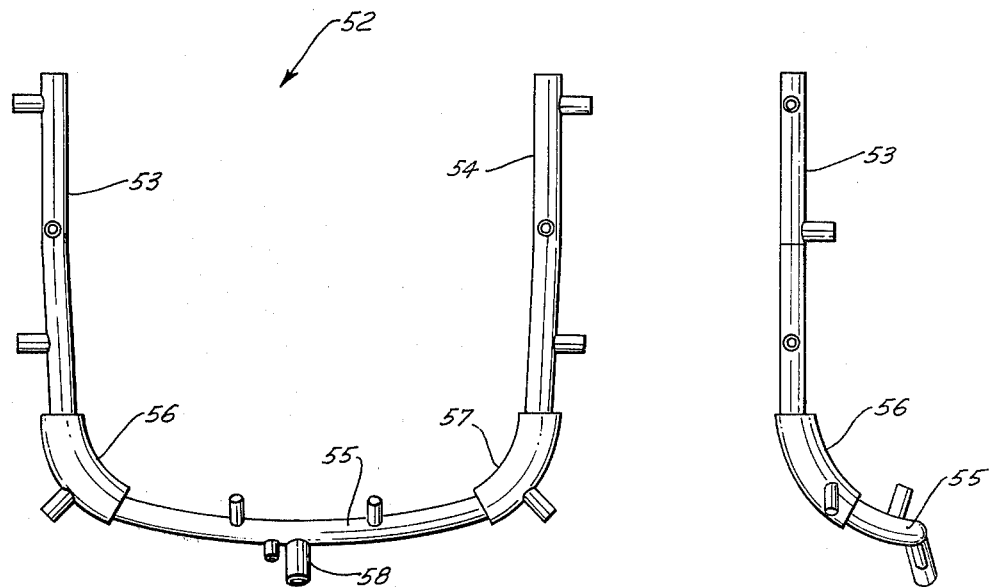
FIG. 11 shows a front view of an evacuating rubber dam frame having coupling means for attaching the vertical arms to the horizontal arm.
FIG. 12 shows a side view of the rubber dam frame of FIG. 11.

FIG. 11 shows a front view of a U-shaped evacuating rubber dam rigid frame 52. This frame is made by attaching the two vertical arms 53 and 54 to the hollow horizontal arm 55 by using the two attachment coupling means 56 and 57, respectively. The method of assembly includes the steps of inserting the lower end of one vertical arm into the upper opening of the first coupling, followed by inserting one end of the horizontal arm into the lower opening of the first coupling. These steps are repeated for the other vertical arm, the second coupling and the horizontal arm. The two couplings 56 and 57 are shown to be elbow joint means. Out-of-round, eliptical, slotted, square or polygonal male and female joints hold all of these elements of the frame in position so that they do not rotate relative to each other. Therefore the frame parts do not get out of proper alignment when the frame is being used during a dental procedure. The hollow horizontal arm has a hollow drainage tube 58 attached to the anterior side, with evacuation openings (not shown) in the posterior side of the horizontal arm. The vertical arms can be removed from the horizontal arm and from the couplings for purposes of internal and/or external cleaning and sterilizing of each of these elements.

FIG. 12 shows a side view, looking at arm 53, of the U-shaped evacuating rubber dam frame 52 shown in FIG. 11. It can be seen how vertical arm 53 is attached by coupling means 56 to horizontal arm 55.

FIG. 13 shows a front view of a U-shaped evacuating rubber dam rigid frame 59. A first horizontal arm 60 is connected to the bottom part of vertical arms 61 and 62; and this first arm 60 is an imperforate solid arm. An example of frame 59 is a metal or plastic frame. A second horizontal arm 63 is a hollow, metal or plastic arm having evacuation openings (not shown) in the posterior side and having a hollow drainage tube 64 in the anterior side. Coupling means 65 and 66 are used to attach the hollow horizontal arm 63 to the imperforate horizontal arm 60. An example of these coupling means 65 and 66 are clips made from metal or plastic. In a first embodiment, the coupling means could be permanently joined to the imperforate horizontal arm 60 of frame 59, so that hollow arm 63 can be removably attached to arm 60. In a second embodiment, the coupling means could be permanently joined to the hollow arm 63, so that the hollow arm can be removably fastened onto frame 59, for example, onto a conventional wire type frame now in use. In a third embodiment, the coupling means could be detachable both from the imperforate horizontal arm 60 and from the hollow horizontal arm 63. In a fourth embodiment, an accessory flexible tube (not shown) could be inserted into an evacuation opening at either end of the hollow horizontal tube 63 for evacuation of more posterior areas of the oral cavity of the dental patient. Hollow drainage tube 64 would then be connected to a saliva ejector suction device.

FIG. 14 shows a section view along section line A-A' of FIG. 13. Coupling means 65 is shown to be a clip for removably fastening together hollow arm 63 with solid arm 60.

FIG. 15 shows front perspective view of the component parts of an assembly for connecting both an extra accessory tube and a hollow drainage tube to a suction device such as a saliva ejector. Attached to hollow arm 67 is hollow drainage tube 68. The lower end of drainage tube 68 is fitted into the upper end of plastic tube 69. The lower end of plastic tube 69 is fitted into the upper end of rubber hose 70. One end of extra accessory tube 71 is fitted into rubber hose 70 between the lower end of plastic tube 69 and the upper end of plastic tube 72. The lower end of plastic tube 72 is fitted into the rubber receptacle 73 on hose 74 which is connected with a dental unit saliva ejector. The extra accessory tube 71 is used to remove fluid from the pocket formed in the area of the most distal, or posteriorly isolated, tooth fitted with a clamp. This tube 71 can be a plastic tube containing a thin wire for enabling the tube to retain its shape.

Figure 16:
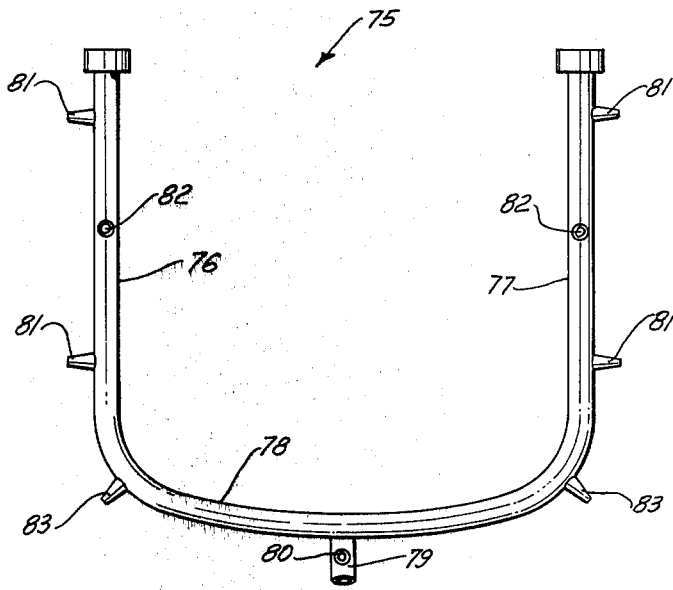
FIG. 16 shows a front view of an evacuating rubber dam frame devoid of barbs on the horizontal arm.

FIG. 16 shows a front view of a U-shaped evacuating rubber dam rigid frame 75, having vertical arms 76 and 77 with hollow horizontal arm 78 connected to the lower part of both vertical arms. Hollow drainage tube 79 has been lowered on the horizontal arm 78 in an inferior direction. A small auxiliary evacuation tube 80 has been added to the top, or superior, surface of drainage tube 79. To this auxiliary evacuation tube 80, a flexible soft tube (not shown) can be attached for evacuating fluid from those areas of the oral cavity of the dental patient that do not readily drain into the collection pocket formed by the rubber dam. On vertical arms 76 and 77 are barbs 81, 82, and 83. Barbs 81 are in the same plane as are vertical arms 76 and 77, while barbs 82 are perpendicular to the plane containing the vertical arms. Barbs 83 are defined as being attached to the lower part of the vertical arms, rather than being attached to the hollow horizontal arm 78. Thus barbs 83 are not part of the horizontal arm 78.

Figure 26:
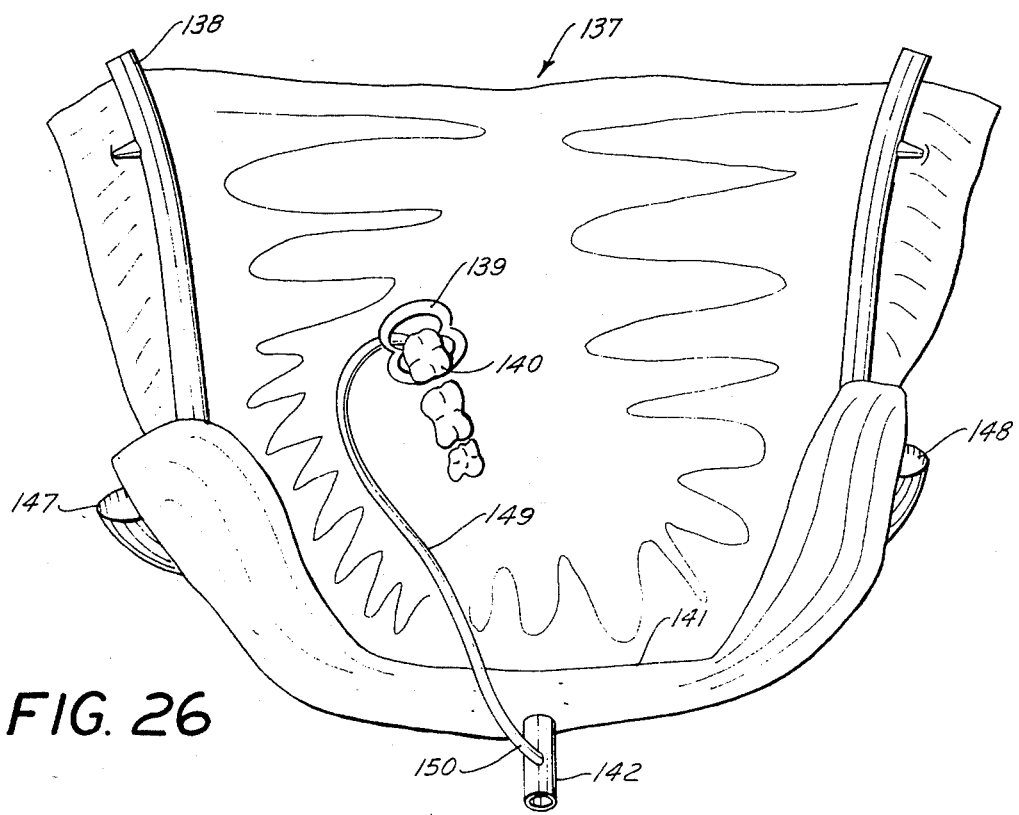
FIG. 26 shows a front view of a rubber dam and an evacuating rubber dam frame, with cupping of the rubber dam.

A comparison of frame 75 in FIG. 16 with frame 21 in FIG. 4 reveals that frame 75 is devoid of any barbs on its horizontal arm 78 that correspond to barbs 29 and 30 on horizontal arm 23 of frame 21. The embodiment shown in FIG. 16 is for use without the cross-over seal described below with reference to FIGS. 27 to 36. There are fewer barbs on frame 75, since there are no barbs on the horizontal arm 78. The hollow drainage tube 79 fits through a hole in the rubber dam and is selfsealing. A hole is to be punched into the lower part of the rubber dam, and the drainage tube 79 is slipped through this hole. The hole in the rubber dam is of slightly smaller inner diameter than is the outer diameter of the drainage tube. Thus the rubber dam when engaging the barbs on the vertical arms provides a cupped selfseal around the drainage tube at the location at which the drainage tube is attached to the hollow horizontal arm. This cupped selfseal is shown in FIG. 26.

Figure 17:
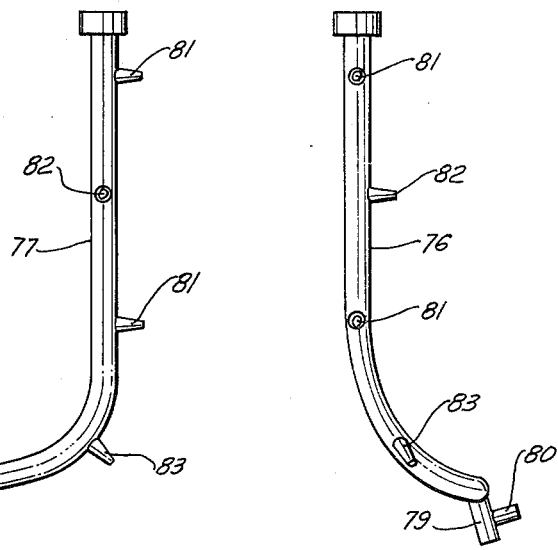
FIG. 17 shows a side view of the rubber dam frame of FIG. 16.

FIG. 17 shows a side view, looking at vertical arm 76, of the U-shaped evacuating rubber dam rigid frame of FIG. 16.

Figure 18:
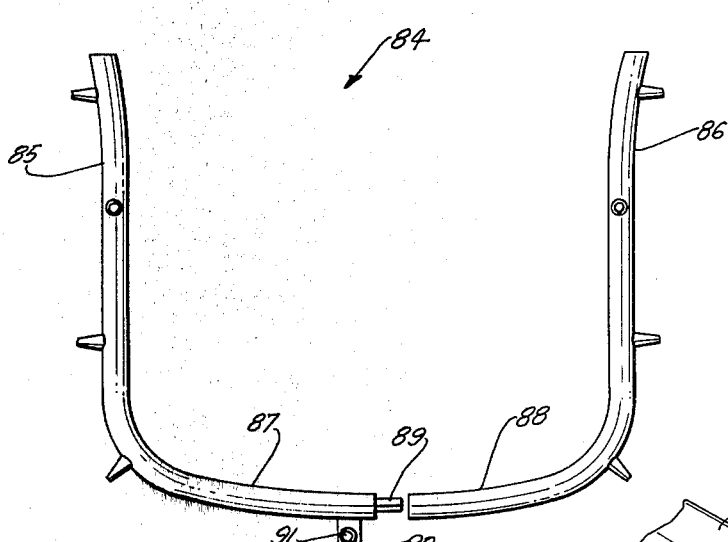
FIG. 18 shows a front view of a jointed evacuating rubber dam frame, disassembled.

FIG. 18 shows a front view of a jointed U-shaped evacuating rubber dam rigid frame 84, having vertical arms 85 and 86. This frame is shown to be disassembled by having arm 85 separated from arm 86. This is done by removing from each other, the left portion 87 of the horizontal arm from the right portion 88 of the horizontal arm, at the joint 89. The left arm portion 87 carries hollow drainage tube 90 to which is attached an auxiliary evacuation tube 91 at the top, or superior, surface of the drainage tube. The joint 89 is a five-sided, or quintagonal, male female sleeve joint.

Figure 19:
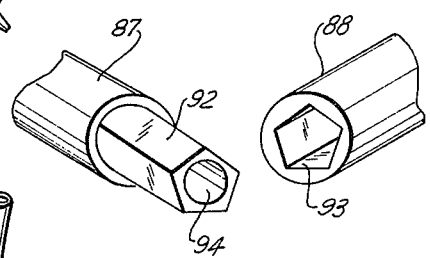
FIG. 19 shows a front perspective view of the disassembled joint of FIG. 18.

FIG. 19 shows a front perspective view of the disassembled joint 89 of FIG. 18. FIG. 19 provides an enlarged view of the quintagonal male component 92 and the quintagonal female component 93 of this sleeve joint. Hollow passageway 94 maintains a continuous open fluid flow channel at the joint 89, so that fluid gathered into the right portion 88 can flow freely into the left portion 87 to be removed through drainage tube 90. While these male female components are shown to be five-sided in shape, the sleeve joint could be of any polygonal shape, provided it functions so as to prevent the two parts of the frame from rotating around relative to each other, after the frame has been assembled.

Figure 20:
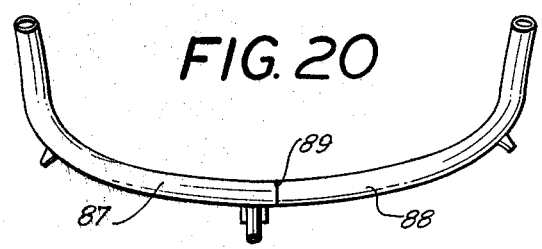
FIG. 20 shows a top view of the jointed evacuating rubber dam frame of FIG. 18, assembled.

FIG. 20 shows a top view of the jointed U-shaped evacuating rubber dam frame 84 of FIG. 18. In FIG. 20 the frame 84 is shown to be assembled by having the left portion 87 of the horizontal arm mated together with the right portion 88 of the horizontal arm, at the joint 89, to provide a unified frame structure.

Figure 21:
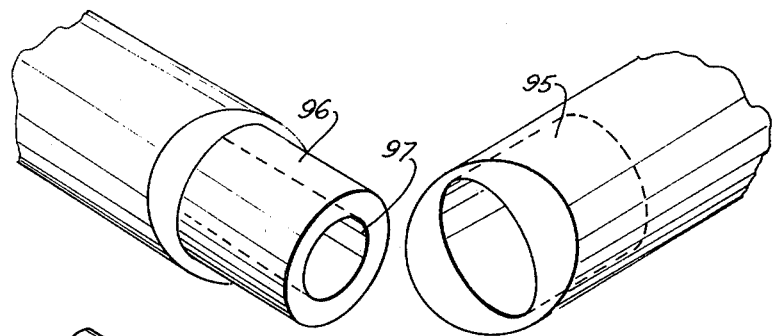
FIG. 21 shows a front perspective view of a disassembled out-of-round sleeve joint.

FIG. 21 shows a front perspective view of a disassembled out-of-round sleeve joint which is to be part of the hollow horizontal arm of an evacuating rubber dam jointed frame similar to frame 84 shown in FIG. 18. The sleeve joint comprises out-of-round hollow female component 95 and out-of-round hollow male component 96 which has hollow passageway 97 for a continuously open fluid flow channel at the joint. This out-of-round joint prevents the two parts of the frame from rotating around relative to each other, after this sleeve joint has been assembled.

Figure 22:
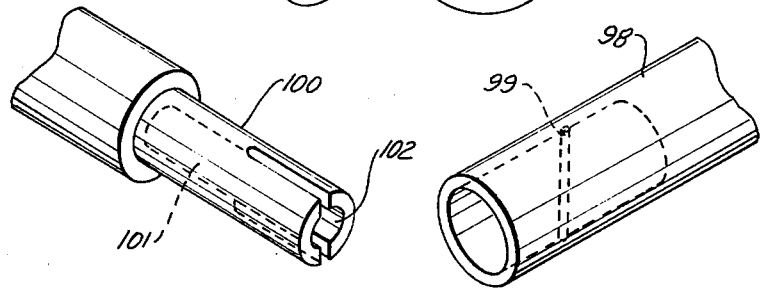
FIG. 22 shows a front perspective view of a disassembled internally slotted sleeve joint.

FIG. 22 shows a front perspective view of a disassembled internally slotted sleeve joint which is to be part of the hollow horizontal arm of an evacuating rubber dam jointed frame similar to frame 84 of FIG. 18. The sleeve joint comprises internally hollow female component 98 having retaining wire 99 to prevent rotation of the joint when assembled. Male component 100 has a hollow passageway 101 as part of its internal slot 102. Assembly of this joint is accomplished by aligning internal slot 102 with retaining wire 99 and then inserting male component 100 into female component 98. Hollow passageway 101 provides a continuously open fluid flow channel at the joint. Retaining wire 99 is thin enough such that it will not block the hollow passageway 101.

Figure 23:
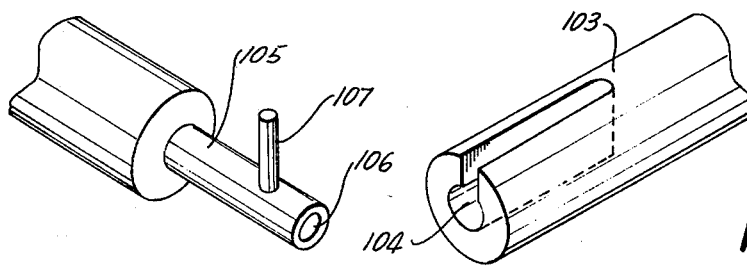
FIG. 23 shows a front perspective view of a disassembled externally slotted sleeve joint.

FIG. 23 shows a front perspective view of a disassembled externally slotted sleeve joint which is to be part of the hollow horizontal arm of an evacuating rubber dam jointed frame similar to frame 84 of FIG. 18. The sleeve joint comprises hollow female component 103 having external slot 104 and hollow male component 105 having hollow passageway 106 and retaining pin 107. Hollow passageway 106 provides a continuously open fluid flow channel at the joint. Retaining pin 107 prevents rotation of the joint when assembled. Assembly of this joint is accomplished by aligning external slot 104 with retaining pin 107 and then inserting male component 105 into female component 103.

Figure 24:
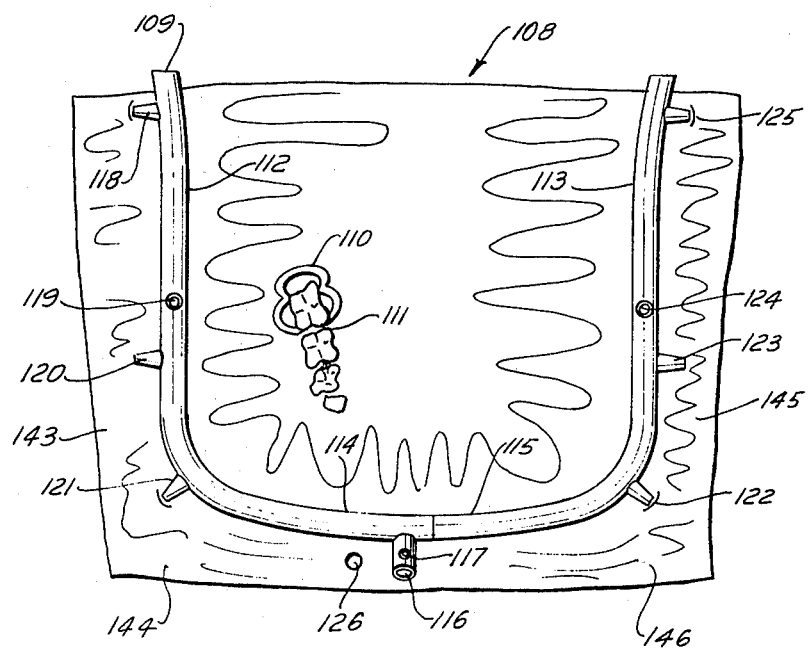
FIG. 24 shows a front view of a rubber dam and a jointed evacuating rubber dam frame, assembled.

FIG. 24 shows a front view of a rubber dam 108 and a jointed U-shaped assembled evacuating rubber dam rigid frame 109 as applied to a dental patient. Rubber dam clamp 110 is clamped around molar 111 to hold the rubber dam 108 firmly in position. In FIG. 24, the rubber dam has not yet been cupped, so as to provide a fluid tight collecting reservoir around the hollow drainage tube and the hollow horizontal arm. The U-shaped assembled frame has two vertical arms 112 and 113 connected by assembled hollow horizontal arm 114. Arm 114 has been assembled at joint 115, and arm 114 carries hollow drainage tube 116 attached thereto. Tube 116 has an auxiliary evacuation tube 117 at the top, or superior, surface thereof. The rubber dam is retained to the frame by being stretched between barb 118 and barb 121 on vertical arm 112 and by being stretched between barb 122 and barb 125 on vertical arm 113. At the lower part of rubber dam 108 is hole 126 through which the hollow drainage tube 116 can be inserted when the dam is later cupped.

Figure 25:
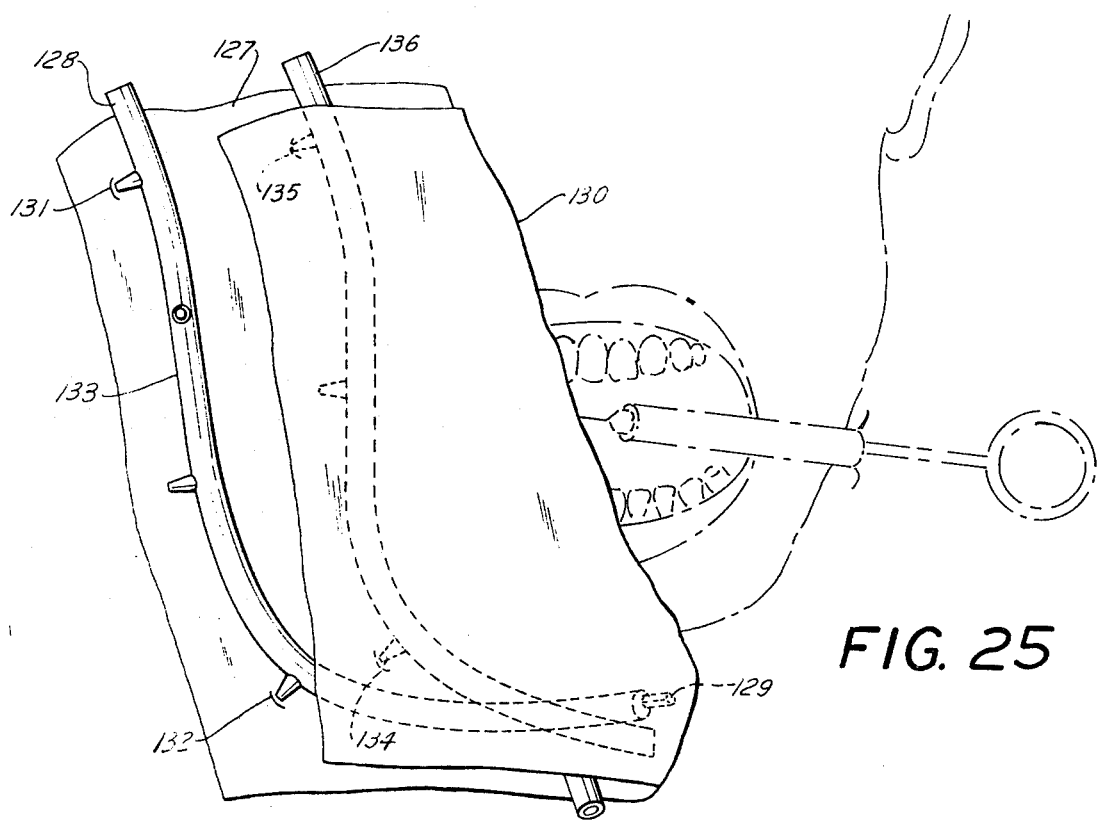
FIG. 25 shows a front view of a rubber dam and a jointed evacuating rubber dam frame, disassembled and folded.

FIG. 25 shows a front view of a rubber dam 127 and a jointed U-shaped disassembled evacuating rubber dam rigid frame 128, as applied to a dental patient. The frame is disassembled at joint 129, thus allowing the side not held by the rubber dam clamp (not shown) to be folded along fold line 130. This permits easy entrance to the mouth of the dental patient for giving additional local anesthetic solution to the patient, or for the taking of X-rays. During the disassembling of the frame, and during, and after, the folding over of the frame plus rubber dam, the dam 127 is retained to the frame 128 by being stretched between barb 131 and barb 132 on vertical arm 133, and by being stretched between barb 134 and barb 135 on vertical arm 136.

FIG. 26 shows a front view of a rubber dam 137 and a U-shaped evacuating rubber dam rigid frame 138 as applied to a dental patient. The frame may be a jointed frame, or may be without a joint in the horizontal arm. Rubber dam clamp 139 is clamped around molar 140 to hold the rubber dam 137 firmly in position. FIG. 26 shows the rubber dam being cupped, so as to provide a fluid tight collecting reservoir 141 around the hollow drainage tube 142 and around the hollow horizontal arm (not shown). The procedure for the cupping of the rubber dam 137 can be understood by referring back to FIG. 24.

In FIG. 24 cupping of dam 108 would be accomplished by inserting hollow drainage tube 116 through hole 126 in the lower part of rubber dam 108. Enough of tube 116 is inserted therethrough such that auxiliary evacuation tube 117 also protrudes through the opening 126 and is free and clear of the rubber dam 108. The four barbs 119, 120, 123 and 124 are used for cupping the dam 108 in the following manner. The area of the dam at the location of arrow 143 is stretched to hook onto barb 120. Then the area of the dam at the location of arrow 144 is stretched to hook onto barb 119. Then the area of the dam at the location of arrow 145 is stretched to hook onto barb 123. Then lastly the area of the dam at the location of arrow 146 is stretched to hook onto barb 124.

Referring again to FIG. 26, it can be seen how the rubber dam can be cupped to provide a fluid tight self-seal around the hollow drainage tube 142. When the area of the rubber dam at location 143 of FIG. 24 is stretched and hooked onto barb 120, an ear-shaped lateral end wall pocket 147 of FIG. 26 is created, which prevents the escape of fluid from that end of the reservoir 141. When the area of the rubber dam at location 145 of FIG. 24 is stretched and hooked onto barb 123, an ear-shaped lateral end wall pocket 148 of FIG. 26 is created, which prevents the escape of fluid from that end of the reservoir 141.

In FIG. 26 it is shown how extra accessory tube 149 is attached at its lower end to auxiliary evacuation tube 150 on hollow drainage tube 142. At its upper end, the extra accessory tube 149 is wedged behind rubber dam clamp 139, and held there to be used to remove fluid from the pocket formed in the area of the most posteriorly isolated tooth 140 fitted with clamp 139. Usually the hollow drainage tube 142 would be attached to a dental saliva ejector in order to quickly remove fluids present in these areas.

In the above examples and in subsequent examples, the hollow drainage tube could be attached to the hollow horizontal arm in the following manner. Starting with a U-shaped frame made, for example, from copper tubing, a hole is drilled into the hollow horizontal arm at the appropriate location. Then a hollow drainage tube made of copper tubing is soldered into this hole in a fluid tight manner. Alternatively a hollow drainage tube made of rigid plastic tubing, or made of flexible rubber hose, could be cemented in place in a fluid tight manner, using a known adhesive, such as an epoxy resin sealer. Additionally the evacuating frame or its components could be fabricated by casting a material such as a metal or plastic into a mold.

FIGS. 27 to 36 show the steps involved in the process of cupping the rubber dam and of forming a cross-over seal by the rubber dam around the hollow drainage tube on the horizontal arm of the evacuating rubber dam frame.

Figure 27:
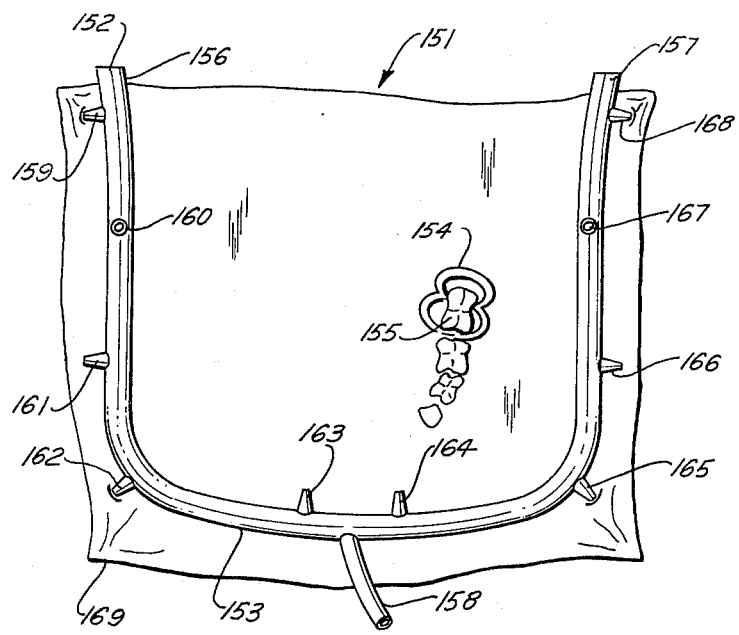
FIG. 27 shows a front view of a rubber dam and an evacuating rubber dam frame.

FIG. 27 shows a front view of a rubber dam 151 and a U-shaped evacuating rubber dam rigid frame 152 as applied to a dental patient. The frame may be a jointed frame, or may be without a joint in the hollow horizontal arm 153. Rubber dam clamp 154 is clamped around molar 155 to hold the rubber dam 151 firmly in position. The U-shaped frame has two vertical arms 156 and 157 connected to hollow horizontal arm 153; and arm 153 has hollow drainage tube 158 attached thereto. The rubber dam is retained and hooked to the frame by being stretched between barb 159 and barb 162 on vertical arm 156 and by being stretched between barb 165 and barb 168 on vertical arm 157. Vertical arms 156 and 157 are parallel to each other and are in the same plane. Barbs 159, 161 and 162 on vertical arm 156, along with barbs 165, 166 and 168 on vertical arm 157, are all in substantially the same plane, which plane also contains vertical arms 156 and 157. Barb 160 on vertical arm 156 and barb 167 on vertical arm 157 are both substantially perpendicular to the plane containing arms 156 and 157. On hollow horizontal arm 153 are barbs 163 and 164 located on the superior, or upper, part of arm 153. The lower left-hand corner area of the rubber dam is that area of the dam at the location of arrow 169.

Figure 28:
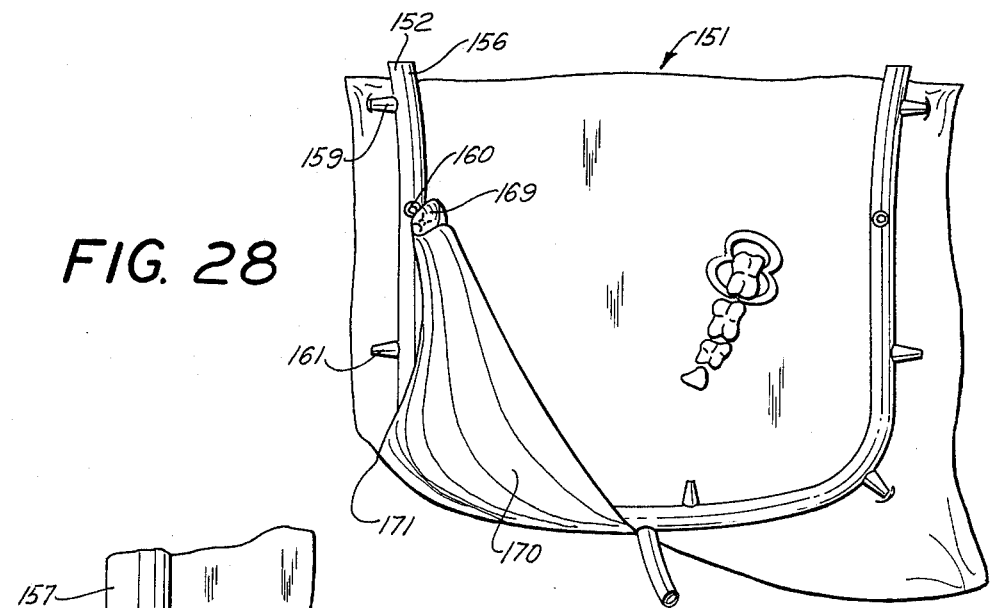
FIG. 28 shows the first step in forming a cross-over seal.

FIG. 28 shows a front view of the rubber dam 151 and the U-shaped evacuating rubber dam rigid frame 152 of FIG. 27. FIG. 28 also shows the next step in the formation of the cross-over seal. The corner area of the rubber dam at the location of arrow 169 of FIG. 27 has been stretched up to and hooked onto barb 160 of vertical arm 156, as shown in FIG. 28. This has created a folded portion 170 in the lower left-hand section of the rubber dam. This also creates a fold line edge at the location of arrow 171.

Figure 29:
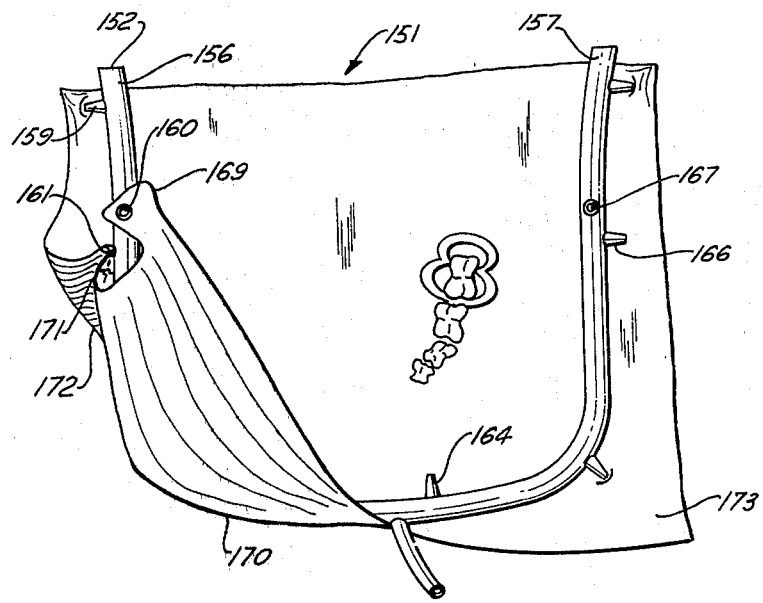
FIG. 29 shows the next step in forming a cross-over seal.

FIG. 29 shows a front view of the rubber dam 151 and the U-shaped evacuating rubber dam rigid frame 152 of FIG. 28. FIG. 29 also shows the next step in the formation of the cross-over seal. The fold line edge at the location of arrow 171 of FIG. 28 has been stretched up to and hooked onto barb 161 of vertical arm 156, as shown in FIG. 29. This creates an ear-shaped lateral end wall pocket 172 which will prevent the escape of fluid from that end of the fluid tight collecting reservoir, which reservoir will finally result from the cupping of the rubber dam and from the formation of the cross-over seal around the hollow drainage tube. The lower right-hand corner area of the rubber dam 151 is that area of the dam at the location of arrow 173. Barb 163 on the horizontal arm is covered by folded portion 170, while barb 164 is unobstructed.

Figure 30:
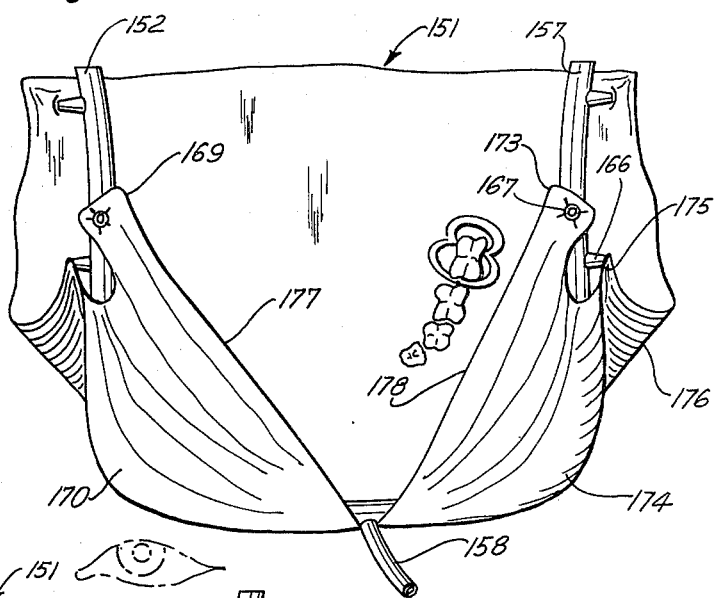
FIG. 30 shows the next step in forming a cross-over seal.

FIG. 30 shows a front view of the rubber dam 151 and the U-shaped evacuating rubber dam rigid frame 152 of FIG. 29. FIG. 30 also shows the next step in the formation of the cross-over seal. A folded portion 174 has been created in the lower right-hand section of the rubber dam. This was accomplished in the following manner. The corner area of the rubber dam at the location of arrow 173 of FIG. 29 has been stretched up to and hooked onto barb 167 of vertical arm 157. This creates folded portion 174 and also creates a fold line edge at the location of arrow 175. This fold line edge at the location of arrow 175 has been stretched up to and hooked onto barb 166 of vertical arm 157. This creates an ear-shaped lateral end wall pocket 176 which will prevent the escape of fluid from the end of the fluid tight collecting reservoir, which reservoir will finally result from the cupping of the rubber dam and from the formation of cross-over seal around the hollow drainage tube. Barb 164 on the horizontal arm has been covered by the folded portion 174. Folded portion 170 has an upper edge which runs between corner area 169 and hollow drainage tube 158. Approximately half way therebetween is central area 177. Folded portion 174 has an upper edge which runs between corner area 173 and hollow drainage tube 158. Approximately half way therebetween is central area 178.

Figure 31:
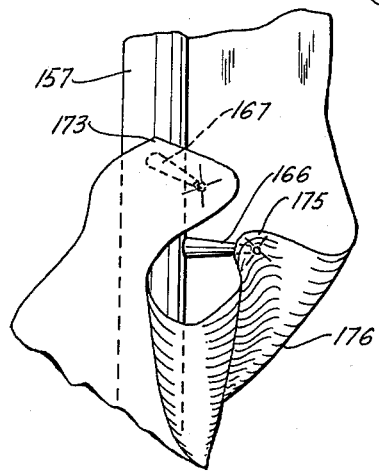
FIG. 31 shows an enlarged front view of part of FIG. 30.

FIG. 31 shows an enlarged front view of the two attached areas, 173 and 175 of FIG. 30, which two areas are hooked onto vertical arm 157 by means of barbs, 167 and 166, respectively. This figure shows in greater detail how the ear-shaped lateral end wall pocket 176 has been created.

Figure 32:
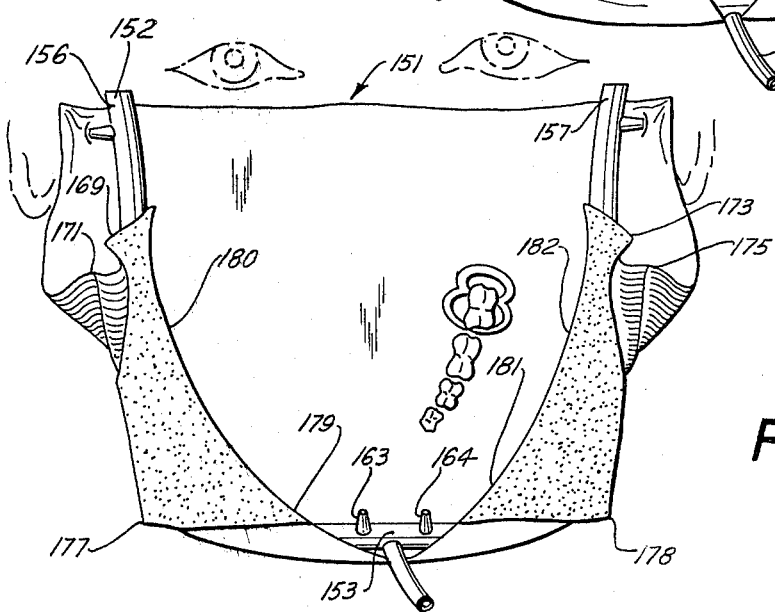
FIG. 32 shows the next step in forming a cross-over seal.

FIG. 32 shows a front view of the rubber dam 151 and the U-shaped evacuating rubber dam rigid frame 152 of FIG. 30. FIG. 32 also shows the next step in the formation of the cross-over seal. Central area 177 of FIG. 30 has been folded and stretched back, so that this area of the dam folds back upon itself. Central area 177 is hooked onto barb 162 (FIG. 7) on vertical arm 156. Note that barb 162 had already been covered with one thickness of rubber dam. Central area 178 of FIG. 30 has been folded and stretched back, so that this area of the dam folds back upon itself. Central area 178 is hooked onto barb 165 (FIG. 27) on vertical arm 157. Note that barb 165 had already been covered with one thickness of rubber dam. Thus it is possible to hook a second layer of rubber dam onto a barb which is already covered with a first layer of rubber dam, without decreasing the effectiveness of the attachment. After central area 177 has been folded back upon itself and then hooked onto barb 162 (FIG. 27), barb 163 on horizontal arm 153 becomes uncovered, and cross-over section 179 is thereby created near to the bottom crease of the fold-line 180. After central area 178 has been folded back upon itself and then hooked onto barb 165 (FIG. 27), barb 164 on horizontal arm 153 becomes uncovered, and cross-over section 181 is thereby created near to the bottom crease of the fold-line 182.

FIG. 33 shows an enlarged front view of the three attached areas, 169 and 171 and 177 of FIG. 32, which three areas are hooked onto vertical arm 156 by means of barbs 160 and 161 and 162, respectively. This figure shows in greater detail how the cross-over section 179 is created near to the bottom crease of the fold-line 180.

FIG. 34 shows a front view of the rubber dam 151 and the U-shaped evacuating rubber dam rigid frame 152 of FIG. 32. FIG. 34 also shows the next step in the formation of the cross-over seal. Previously as shown in FIG. 32, the cross-over section 179 was near to the bottom crease of the fold-line 180 on the left side of the hollow drainage tube 158. Now the cross-over section 179 has been stretched to the right, so as to cross over to the right side of the hollow drainage tube 158 in order to be hooked onto barb 164 on the right side of tube 158. In order to traverse this distance from being at the left side of the tube 158 to being at the right side of tube 158, cross-over section 179 must pass around barb 163. Preferably cross-over section 179 passes around the front of barb 163 in order to be wrapped very tightly over the upper surface of the hollow drainage tube 158 and over that portion of the hollow horizontal arm to which the tube 158 is attached.

FIG. 35 shows a front view of the rubber dam 151 and the U-shaped evacuating rubber dam rigid frame 152 of FIG. 34. FIG. 35 also shows the last step in the cupping of the rubber dam, so as to provide a fluid tight collecting reservoir, and in the formation of the cross-over seal around the hollow drainage tube 158. Previously as shown in FIG. 34, the cross-over section 181 was near to the bottom crease of the fold-line 182 on the right side of the hollow drainage tube 158. Now the cross-over section 181 has been stretched to the left, so as to cross over to the left side of the hollow drainage tube 158 in order to be hooked onto barb 163 (FIG. 34) on the left side of the tube 158. In order to traverse this distance from being at the right side of tube 158 to being at the left side of tube 158, cross-over section 181 must pass around barb 164 (FIG. 36), to which cross-over section 179 had previously been hooked. Preferably cross-over section 181 passes around the front of barb 164 (FIG. 36) and around the front of cross-over section 179, in order to be wrapped very tightly over the upper surface of the hollow drainage tube 158 and over that portion of the hollow horizontal arm to which the tube is attached.

FIG. 36 shows an enlarged front view of the cross-over seal around hollow drainage tube 158 of FIG. 35. In this view it can be seen how the cross-over seal fits intimately around the hollow drainage tube 158 and around that part of the front of the horizontal arm 153 to which tube 158 is attached. This cross-over seal fits so tightly that a fluid tight collecting reservoir is created encompassing the hollow drainage tube and the hollow horizontal arm. This is due to the fact that the left side cross-over section 179 had been stretched and hooked onto barb 164 on the right side of tube 158, after which, right side cross-over section 181 has been stretched and hooked onto barb 163 on the left side of tube 158. This cross-over seal around the front part of hollow horizontal arm 153 does not in any manner interfere with the proper functioning of the evacuation openings in the rear of the horizontal arm for gathering in fluid collected by the rubber dam, during a dental procedure.

Figure 37:
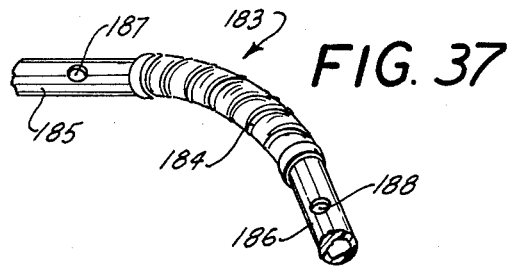
FIG. 37 shows a top view of a flexible joint for frame.

FIG. 37 shows a top view of a flexible joint 183 for folding a U-shaped evacuating rubber dam frame (not shown). The flexible joint 183 comprises a flexible hollow conduit 184 connecting rigid hollow tubing 185 with rigid hollow tubing 186. In actuality, rigid tubing 185 would be part of the left portion of the hollow horizontal arm of a U-shaped frame, while rigid tubing 186 would be part of the right portion of the hollow horizontal arm of a U-shaped frame. The hollow drainage tube (not shown) would be attached to either the right or the left portion. The flexible conduit 184 is shown to be curved indicating the manner by which the U-shaped frame could be folded back without the necessity of first disassembling the frame. Openings 187 and 188 are each used to accommodate one end of a stabilizer bar used to prevent the undesired curvature of flexible conduit 184, when a straight line connection is necessary between tubings 185 and 186. An example of the flexible conduit 184 is the type of flexible tubing used for the spout on a portable gasoline can. The flexible conduit 184 has the inherent stability to prevent the two parts of the U-shaped frame from rotating around relative to each other, even when the flexible conduit is being curved in order to fold back the frame. At all times, the flexible conduit will maintain a continuous open fluid flow channel at the joint, so that fluid gathered into one portion can freely flow into which ever other portion contains the drainage tube removal means.

Figure 38:
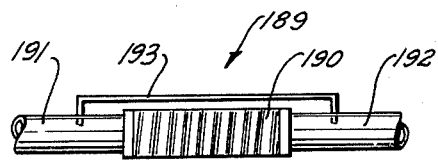
FIG. 38 shows a front view of a flexible joint for a frame.

FIG. 38 shows a front view of a flexible joint 189, which compriss a flexible hollow conduit 190 connecting rigid hollow tubing 191 with rigid hollow tubing 192. One end of stabilizer bar 193 is inserted into the opening in the top of tubing 191, while the other end is inserted into the opening in the top of tubing 192. These openings are analogous to openings 187 and 188 of FIG. 37. The stabilizer bar insures a straight line connection between the tubings 191 and 192, by preventing curvature of the flexible conduit 190.

Figure 39:
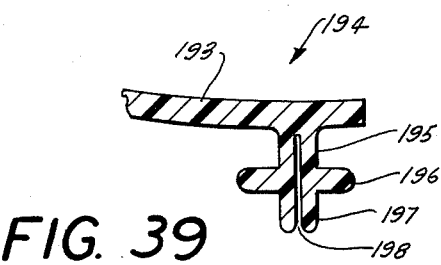
FIG. 39 shows an enlarged cross section of an insert snap.

FIG. 39 shows an enlarged cross section of the insert snap 194 located at each end of the stabiler bar 193 of FIG. 38. The insert snap is inserted into the opening in the top of the hollow rigid tubing, and detachably anchors the stabilizer bar into position. The insert snap comprises a narrow neck portion 195, connecting the snap 194 to the bar 193. There is an expanded middle portion 196 for anchoring the bar into position when in use with a flexible joint. There is a narrow bottom portion 197 containing the beginning of an open chamber 198. Open chamber 198 allows the insert snap to be compressed whenever the snap is inserted into, or is removed from, the hollow rigid tubing. Otherwise the insert snap would assume the expanded arrangement shown in FIG. 39.

Figure 40:
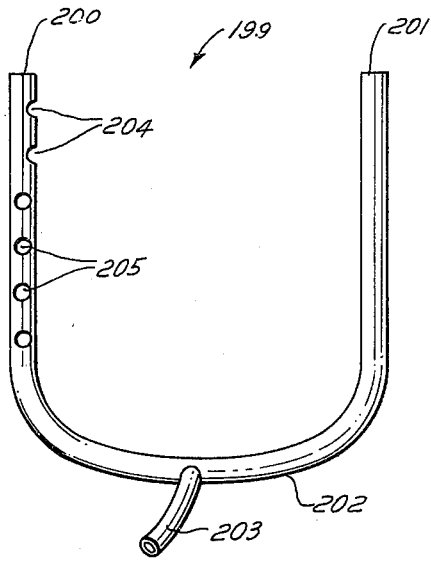
FIG. 40 shows a front view of an evacuating rubber dam frame.

FIG. 40 shows a front view of a U-shaped evacuating rubber dam rigid frame 199. This U-shaped frame has two hollow vertical arms 200 and 201 connected to hollow horizontal arm 202; and arm 202 has hollow drainage tube 203 attached thereto. Horizontal arm 202 has evacuation openings (not shown) in the rear thereof for gathering in fluid collected by a rubber dam. All of the arm members are continuously connected together. Left arm 200 is shown containing means 204 and 205 for removal of aerosol spray mists. Removal means 204 are additional evacuation holes in the inner side wall surface of arm 200 which open toward the right arm 201. Removal means 205 are additional evacuation holes in the front wall surface of arm 200 which open away from the face of a dental patient. These additional openings are positioned into those surfaces of the frame which face the work area. Corresponding additional openings could also be present in arm 201, and are omitted here for simplification purposes. When the hollow drainage tube is connected to a suction device, these additional evacuation openings function to more completely evacuate aerosol spray mists from the work area.

Figure 41:
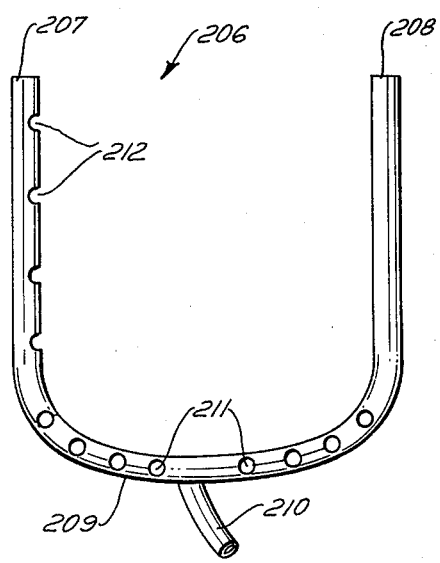
FIG. 41 shows a rear view of an evacuating rubber dam frame.

FIG. 41 shows a rear view of a U-shaped evacuating rubber dam rigid frame 206. Frame 206 has two hollow vertical arms 207 and 208 continuously connected to hollow horizontal arm 209; and arm 209 has hollow drainage tube 210 attached thereto. Horizontal arm 209 has evacuation openings 211 in the rear thereof for gathering in any fluid collected by a rubber dam. Left arm 207 is shown containing means 212 for removal of aerosol spray mists. Removal means 212 are additional evacuation holes in the inner side wall surface of arm 207 which open toward the right arm 208 and which face the work area. Corresponding additional openings could also be present in arm 208.

Figure 42:
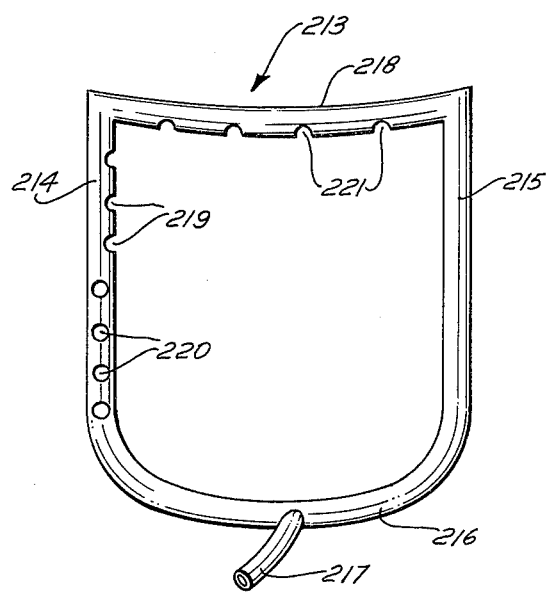
FIG. 42 shows a front view of an evacuating rubber dam frame.

FIG 42 shows a front view of a U-shaped evacuating rubber dam frame 213. Frame 213 has two hollow rigid vertical arms 214 and 215 connected to a hollow rigid lower horizontal arm 216; and lower arm 216 has hollow drainage tube 217 attached thereto. Horizontal arm 216 has evacuation openings (not shown) in the rear thereof for gathering in any fluid collected by a rubber dam. Vertical arms 214 and 215 are connected at the upper end to a superior, substantially horizontal, arm 218. All of the arm members are continuously connected together. Superior arm 218 can be rigid; or it can be a flexible tube, such as a rubber hose.

In an embodiment wherein the lower rigid arm 216 contains a joint means (not shown) and wherein the superior arm 218 is flexible, it would be possible that the evacuating rubber dam frame could be folded. This would allow the side of the frame not retained by a rubber dam clamp, to be bent back upon itself. Hence this combination of a mostly rigid and a partly flexible type of frame, having joint means in the rigid part, allows frames of any shape to be folded.

Left arm 214 is shown containing means 219 and 220 for removal of aerosol spray mists. Removal means 219 are additional evacuation holes in the inner side wall surface of arm 214 which open toward the right arm 215. Removal means 220 are additional evacuation holes in the front wall surface of arm 214 which open away from the face of a dental patient. Superior arm 218 contains means 221 for removal of aerosol spray mists. Removal means 221 are additional evacuation holes in the inferior side wall surface of superior arm 218 which open toward the lower arm 216. These additional openings are positioned into those surfaces of the frame which face the work area. Corresponding additional openings could also be present in arm 215.

Figure 43:
FIG. 43 shows a front view of additional evacuation holes.

FIG. 43 shows a front view of the additional evacuation holes which are shown from the side in FIG. 42. These openings are representative of holes 219 or 221.

The evacuation rubber dam frame of the present invention has the following advantages. The rubber dam frame will support a rubber dam adjacent to the mouth of a dental patient during a dental procedure, and will simultaneously evacuate through the frame, fluids which are adjacent to the frame, after these fluids had first been collected by the rubber dam. The frame holds the rubber dam in place so that the rubber dam does not move into the field of dental interest. The frame and the rubber dam function in combination to form a leakproof system, such that the frame promptly removes fluids collected by the rubber dam; and the frame prevents the overflow of fluids from the portion of the mouth isolated by the rubber dam, onto the patient. Where the evacuating rubber dam frame is comprised of hollow parts detachably connected together, these parts can be removed from one another for purposes of internal and/or external cleaning and sterilizing thereof. Where the evacuating rubber dam frame is a jointed frame, this frame may be flexibly folded or may be disassembled even while being utilized to support a rubber dam adjacent to the mouth of a dental patient. This allows the side of the frame not being held by the rubber dam clamp to be folded back upon itself. This permits easy entrance to the mouth of the dental patient for giving additional local anesthetic solution to the patient, or for the taking of X-rays. Where the evacuating rubber dam frame contains means for removal of aerosol spray mists, this can help to effectively reduce the inhalation of bacteria containing aerosol spray mists by the patient and others nearby.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

What is claimed is:

1. An evacuating rubber dam frame for supporting a rubber dam adjacent to the mouth of a dental patient comprising
   a frame containing a hollow portion,
   said hollow portion having means for gathering in any fluid collected by said rubber dam,
   means for removal of fluid gathered into said hollow portion, and
   said frame being a U-shaped member which is contoured to be retractable against a portion of the face of said dental patient surrounding said patient's mouth.

2. The evacuating rubber dam frame of claim 1, further comprising means for retention of a rubber dam.

3. The evacuation rubber dam frame of claim 1, further comprising joint means for folding said frame.

4. The evacuation rubber dam frame of claim 1, further comprising means for removal of aerosol spray mists.

5. An evacuating rubber dam frame for supporting a rubber dam adjacent to the mouth of a dental patient comprising
   two vertical arms,
   a hollow horizontal arm connected to the bottom part of both of said vertical arms,
   said hollow horizontal arm having at least one evacuation opening in the rear of said horizontal arm for gathering in any fluid collected by said rubber dam,
   a hollow drainage tube attached to one of said arms for removal of fluid gathered into said hollow horizontal arm,
   and said frame being a U-shaped member which is contoured to be retractable against a portion of the face of said dental patient surrounding said patient's mouth.

6. The evacuation rubber dam frame of claim 5, wherein said hollow drainage tube is attached to said hollow horizontal arm.

7. The evacuating rubber dam frame of claim 5, wherein said hollow horizontal arm has more than one evacuation opening in the rear of said horizontal arm.

8. The evacuating rubber dam frame of claim 5, wherein one of said vertical arms is hollow,
   wherein said hollow drainage tube is attached to said hollow vertical arm, and
   wherein said hollow drainage tube is a suction drainage tube.

9. The evacuating rubber dam frame of claim 5, wherein said hollow horizontal arm is a rigid horizontal arm.

10. The evacuating rubber dam frame of claim 5, wherein each of said two vertical arms is a hollow vertical arm.

11. The evacuating rubber dam frame of claim 5, wherein each of said two vertical arms is a rigid vertical arm.

12. The evacuating rubber dam frame of claim 6, wherein said hollow drainage tube is attached to the front of said hollow horizontal arm and positioned substantially opposite to said evacuating opening.

13. The evacuating rubber dam frame of claim 6, wherein said hollow drainage tube is a rigid drainage tube located in the front central portion of said hollow horizontal arm.

14. The evacuating rubber dam frame of claim 5, wherein each of said two vertical arms is continuously connected to said hollow horizontal arm to form a unitary frame.

15. The evacuating rubber dam frame of claim 14, wherein each of said two vertical arms is a hollow arm.

16. The evacuating rubber dam frame of claim 14, wherein each of said two vertical arms is a solid arm.

17. The evacuating rubber dam frame of claim 5, wherein at least one of said two vertical arms is a solid arm.

18. The evacuating rubber dam frame of claim 5, wherein at least one of said two vertical arms is of a thickness different from that of said hollow horizontal arm.

19. The evacuating rubber dam frame of claim 5, further comprising attachment means for removably coupling each of said two vertical arms to said hollow horizontal arm.

20. The evacuating rubber dam frame of claim 19, wherein said attachment means is selected from the group comprising screw thread means, friction joint means, and elbow joint means.

21. The evacuating rubber dam frame of claim 5,
    wherein said two vertical arms are in one plane and said hollow horizontal arm is in the same plane as said two vertical arms,
    and wherein the ends of said vertical arms remote from said horizontal arm are bent laterally outwardly from one another.

22. The evacuating rubber dam frame of claim 5,
    wherein said two vertical arms are in a first plane and said hollow horizontal arm is curved outwardly away from said first plane, and
    wherein the ends of said vertical arms remote from said horizontal arm are bent laterally outwardly from one another.

23. The evacuating rubber dam frame of claim 5, further comprising means for retention of a rubber dam.

24. The evacuating rubber dam frame of claim 6, further comprising barbs on said two vertical arms and barbs on said hollow horizontal arm.

25. The evacuating rubber dam frame of claim 24,
    wherein said barbs are so structured and arranged on said two vertical arms and in said hollow horizontal arm that said rubber dam when engaging said barbs provides a crossover seal around said hollow drainage tube at the location at which said hollow drainage tube is attached to said hollow horizontal arm.

26. The evacuating rubber dam frame of claim 6, further comprising barbs on said two vertical arms for engaging said rubber dam.

27. The evacuating rubber dam frame of claim 26, wherein said rubber dam has a hole in the lower portion thereof positioned to receive said hollow drainage tube and said hole being of slightly smaller inner diameter than the outer diameter of said hollow drainage tube, and wherein said barbs are so structured and arranged on said two vertical arms, that when said hollow drainage tube is inserted through said hole in said rubber dam, that said rubber dam when engaging said barbs provides a cupped selfseal around said hollow drainage tube at the location at which said hollow drainage tube is attached to said hollow horizontal arm.

28. The evacuating rubber dam frame of claim 5, wherein said hollow horizontal arm further comprises joint means for folding said frame.

29. The evacuating rubber dam frame of claim 28, wherein said joint means is a flexible joint means.

30. The evacuating rubber dam frame of claim 29, wherein said flexible joint means is selected from the group comprising a pivot joint, an elastic joint, and a flexible conduit joint.

31. The evacuating rubber dam frame of claim 28, wherein said joint means is an assembly joint means for assembling and disassembling said frame.

32. The evacuating rubber dam frame of claim 31, wherein said assembly joint means is a sleeve joint selected from the group comprising an out-of-round sleeve joint, a polygonal sleeve joint, an internally slotted sleeve joint and an externally slotted sleeve joint.

33. The evacuating rubber dam frame of claim 5, further comprising means for removal of aerosol spray mists.

34. The evacuating rubber dam frame of claim 33, wherein said means for removal comprises additional evacuation openings in at least one of said two vertical arms, said additional evacuation openings being positioned into said at least one vertical arm for evacuating aerosol spray mists.

35. An evacuating rubber dam frame for supporting a rubber dam adjacent to the mouth of a dental patient comprising two vertical arms, an imperforate horizontal arm connected to the bottom part of both of said vertical arms, a hollow horizontal arm having at least one evacuation opening in the rear of said hollow horizontal arm for gathering in any fluid collected by said rubber dam, a hollow drainage tube attached to said hollow horizontal arm for removal of fluid gathered into said hollow horizontal arm, coupling means for attaching said hollow horizontal arm to said imperforate horizontal arm, and said frame being a U-shaped member which is contoured to be retractable against a portion of the face of said dental patient surrounding said patient's mouth.

* * * * *